United States Patent [19]
Jensen

[11] Patent Number: 5,242,835
[45] Date of Patent: Sep. 7, 1993

[54] METHOD AND APPARATUS FOR DETERMINING THE CONCENTRATION OF OXYGEN

[75] Inventor: Niels-Henrik Jensen, Farum, Denmark

[73] Assignee: Radiometer A/S, Copenhagen, Denmark

[21] Appl. No.: 917,905

[22] Filed: Jul. 21, 1992

Related U.S. Application Data

[63] Continuation of Ser. No. 125,407, Nov. 25, 1987, abandoned.

[30] Foreign Application Priority Data

Nov. 3, 1987 [DK] Denmark .................... 5761/87

[51] Int. Cl.$^5$ ........................................ G01N 21/63
[52] U.S. Cl. .................... 436/136; 436/68; 436/167; 436/169; 436/172; 422/82.05; 422/82.06; 356/39; 250/458.1; 250/459.1
[58] Field of Search ............... 436/68, 136, 138, 167, 436/169, 172; 422/82.05, 91, 82.06; 356/39–41; 250/458.1, 459.1; 128/633, 634, 654, 665

[56] References Cited

U.S. PATENT DOCUMENTS

| | | | |
|---|---|---|---|
| Re. 31,879 | 5/1985 | Lubbers et al. | 436/133 |
| 3,612,866 | 10/1971 | Stevens | 250/71 |
| 3,619,061 | 11/1971 | Mitchell | 356/85 |
| 4,399,099 | 8/1983 | Buckles | 422/58 |
| 4,476,870 | 10/1984 | Peterson et al. | 128/634 |
| 4,542,987 | 9/1985 | Hirschfeld | 356/44 |
| 4,576,173 | 3/1986 | Parker et al. | 128/633 |
| 4,592,361 | 6/1986 | Parker et al. | 128/633 |
| 4,810,655 | 3/1989 | Khalil et al. | 436/136 X |

OTHER PUBLICATIONS

Chemical Abstracts, vol. 94, No. 11, Abstract No. 83264d, Maillard et al. (1981).
Spellane, et al., "Porphyrins and the Electronic Spectra and Four-Orbital Energies of Free-Base, Zinc, Copper, and Palladium Tetrakis (perfluorophenyl)Porphyrins", 1986, *Inorg. Chem.* 19, pp. 386–391.
IUPAC Commission on Photochemistry, "Glossary of Terms used in Photochemistry", Parts I, II and III, EPA Newsletter, Nov. 1985, Mar. 1986, Jul. 1986, respectively.
I. S. Longmuir and J. A. Knopp, "Measurement of tissue oxygen with fluorescent probe," Journal of Applied Physiology, 41, 4, 1976.
I. Bergman, *Nature*, 218, 1968, p. 376.
W. M. Vaughan and G. Weber, "Oxygen Quenching and Pyrenebutyric Acid Fluorescence in Water. A Dynamic Probe of the Microenvironment," *Biochemistry*, vol. 9, No. 3, Feb. 3, 1970, pp. 464–473.
P. R. Ogilby et al., "The Photosensitized Production of Singlet Molecular Oxygen ($^1O_2$) in a Solid Organic Polymer Glass: A Direct Time-resolved Study,": *J. Am. Chem. Soc.*, 109, 1987, pp. 4746–4747.
M. Kasha, "Singlet O vol. I," CRC Press, 1985, pp. 1–11.

*Primary Examiner*—James C. Housel
*Assistant Examiner*—Jeffrey R. Snay
*Attorney, Agent, or Firm*—Bryan, Cave

[57] ABSTRACT

The concentration of molecular oxygen in a sample is determined by exciting oxygen molecules of the sample from the electronic ground state to the excited $^1\Delta_g$ state (excited singlet state), measuring a 1270-nm luminescence characteristic of the excited oxygen molecules (singlet oxygen) and correlating the luminescence characteristic measured with the concentration of molecular oxygen in the sample. Normally, the 1270-nm luminescence characteristic is the 1270-nm luminescence intensity. Preferably, the oxygen molecules are excited by being subjected to diffusion contact with a sensitizer such as a porphyrin or a porphyrin-related compound, e.g. a transition metal complex of a porphyrin. The sensitizer is brought into an oxygen-exciting electronic state by absorption of electromagnetic radiation such as light, the oxygen-exciting electronic state optionally being adapted to the measuring system employed by means of a quencher such as a substituted polyene. The sensitizer may be present in an organic solvent or a polymer such as polyvinylchloride. The oxygen-containing sample is preferably a sample of biological origin such as a blood sample.

42 Claims, 7 Drawing Sheets

METHOD AND APPARATUS FOR DETERMINING THE CONCENTRATION OF OXYGEN

This is a continuation of U.S. application Ser. No. 07/125,407, filed Nov. 25, 1987, now abandoned, which is incorporated by reference herein.

The present invention relates to a method of determining the concentration of molecular oxygen in a sample and to systems for determining said concentration.

BACKGROUND OF THE INVENTION

It has been possible for some years to determine the concentration of molecular oxygen in a sample by using optical methods based on luminescence quenching. In general, these methods comprise measuring the luminescence intensity and/or the luminescence lifetime of a suitable luminophore, the luminophore being in contact with an oxygen-containing sample and being exposed to illumination.

The basic feature of luminescence quenching is the deactivation of the luminescing excited electronic state of the luminophore taking place on collision with oxygen molecules. As the average number of luminophore molecules in the excited electronic state is reduced by the interaction with the oxygen molecules, the luminescence intensity and the excited state lifetime of the luminophore are reduced. The magnitude of the reduction is connected with the number of oxygen molecules in contact with the luminophore through the Stern-Volmer equation $$M^{\circ}/M = 1 + K_{SV}[O_2]$$

see e.g. IUPAC Commission on Photochemistry, and "Glossary of Terms used in Photochemistry, part III", *EPA Newsletter*, July 1986. $M^{\circ}$ and $M$ of the above equation designate the luminescence intensity or the excited state lifetime of the luminophore in the absence and presence of oxygen, respectively. $[O_2]$ designates the concentration of molecular oxygen corresponding to the M-value measured. $K_{SV}$ is the socalled Stern-Volmer constant explained in the above reference. By using this equation and correlating it to samples of known oxygen concentration, it is possible to determine the oxygen concentration of a sample.

A great deal of research has been going on throughout the years to develop and improve the luminescence quenching method of determining oxygen concentrations. The aim of the research has among other things been to find useful luminophore substances, to improve the contact between the luminophore and the oxygen molecules and to develop improved devices suited for specific uses.

Aromatic molecules have been found useful as luminophore substances by several researchers (Stevens in U.S. Pat. No. 3,612,866, Stanley et al in U.S. Pat. No. 3,725,658). Specific examples of useful luminophores are pyrene butyric acid (Longmuir, I. S. and Knopp J. A., "Measurement of tissue oxygen with a fluorescent probe", *Journal of applied physiology*, 41, 4, USA 1976), porphyrins and derivatives thereof (Kahil in international publication No. WO 87/00023) and inorganic metal complexes (Bacon, J. R. and Demas, J. N. in UK patent application No. 2,132,348). The luminophore may be embedded in a matrix such as a glass matrix as disclosed by Bergman, I., *Nature* 218, 1968, p. 376, or a polymer matrix as disclosed by Kahil, supra, or Bacon, supra. The method of luminescence quenching has been employed in a variety of systems. For instance, fibre optic probes containing a dye and being implantable in human body tissue are disclosed by Peterson et al. in U.S. Pat. No. 4,476,870.

Further, the optical quenching method is disclosed inter alia in:

Vauthan, W. M. and Weber, G., "Oxygen Quenching and Pyrenebutyric Acid Fluorescence in Water. A Dynamic Probe of the Microenvironment", *Biochemistry*, Volume 9, No. 3, Feb. 3, 1970, pp. 464–473.

Buckles, R. G. in U.S. Pat. No. 4,399,099,

Murray, R. C., Jr. and Lefkowitz, S. M. in European Patent Publication No. 0 190 829, Hirschfeld in U.S. Pat. No. 4,542,987, Lübbers et al in U.S. reissued patent No. Re. 31,879, Hesse, H. C. in DD patent application No. 106086 and Murray, R. C., Jr. and Lefkowitz, S. M. in European patent publication No. 0 190 830.

The present invention provides a new method of optically determining the concentration of molecular oxygen present in a sample.

When using the method of the invention, the concentration of molecular oxygen in a sample is determined by exciting oxygen molecules of the sample from the electronic ground state to the excited $^1\Delta_g$-state (excited singlet state), measuring a 1270-nm luminescence characteristic of the excited oxygen molecules and correlating the luminescence characteristic measured with the concentration of molecular oxygen in the sample.

In contrast to the basic principle of the known optical methods, i.e. measuring light emitted from another substance than oxygen, the present invention is based on the principles of determining the concentration of oxygen in a sample by measuring the light emission at 1270 nm from oxygen. The method of the present invention has the same advantages as the known optical methods (for example, the oxygen is not consumed in the method of the invention), but is superior to the known methods from a practical measuring point of view. More specifically, the present method is specific to oxygen as the signal obtained at 12170 nm is substantially attributable to oxygen and generally less sensitive to interference from substances other than oxygen. This is in contrast to the known methods based on luminescence quenching, wherein the intensity or the lifetime reductions caused by other substances cannot be distinguished from the oxygen-derived signal changes. Also, the luminescence signal obtained at 1270 nm increases with increasing concentrations of oxygen starting at essentially zero in the absence of oxygen. This makes amplification of the 1270-nm signal obtained in the presence of oxygen by the method of the invention possible. In contrast, the oxygen-induced signal reduction of the known luminescence quenching methods does not permit any signal amplification. Moreover, calibration of the measurement method according to the present invention is more simple than calibration of the known luminescence quenching methods, as the establishment of a standard curve may be based on only one known oxygen concentration in addition to the reference value which is implicitly known (zero in the absence of oxygen).

Examples of publications which discuss the 1270-nm emission from singlet oxygen are:

Parker et al in U.S. Pat. No. 4,592,361,

Parker et al in U.S. Pat. No. 4,576,173,

Ogilby, P. R. et al, "The Photosensitized Production of Singlet Molecular Oxygen ($^1\Delta_g O_2$) in a Solid Organic Polymer Glass: A Direct Time-resolved Study", *J. Am. Chem. Soc.*, 109, 1987, pp. 4746–4747.

THEORETICAL BACKGROUND OF THE INVENTION

The excitation of oxygen molecules so as to form the excited singlet state or the singlet oxygen, as it is also termed, cannot be achieved with any significant efficiency by direct absorption of electromagnetic radiation, and the oxygen molecules must therefore be excited in another way. Conveniently, excitation of the oxygen molecules is performed by means of a socalled sensitizer which is a compound or a composition which, when receiving energy in a suitable form, i.e. electromagnetic radiation, may be brought into an excited electronic state (sensitizing excited state) capable of exciting molecular oxygen from the electronic ground state to the excited singlet state.

The mutual ordering of the electronic states of the sensitizer and the molecular oxygen can be depicted in a Jablonski diagram, as illustrated in FIG. 5, where a few of the lower relevant electronic states are represented. By absorption of light, the ground state ($S_0$) of the sensitizer may be excited to the first excited singlet state ($S_1$) or to the second or higher excited singlet state ($S_2$, $S_3$, . . .). These excited singlet states may be deactivated to the ground state by non-radiated internal conversion (as illustrated by wavy arrows) or by fluorescence (as illustrated by straight arrows), or they may undergo socalled intersystem crossing so as to form excited triplet states ($T_1$, $T_2$, . . .), the most common intersystem crossing being illustrated by the wavy arrow from $S_1$ to $T_1$. The excited triplet states may return to the ground state by phosphorescence (straight arrow from $T_1$ to $S_o$) or by non-radiative processes including quenching. In the present context, the quenching (i.e. the deactivation) of the excited sensitizer by molecular oxygen (wavy arrow from $T_1$ to $^1\Delta_g$) with the resulting formation of singlet oxygen is the interesting feature and it will therefore be discussed in detail below.

The sensitizer is normally "embedded" in a "matrix" (although, as explained below, it may also be embedded in the sample). The term "embedded in" as used in the present specification and claims is intended to embrace any appropriate way of containing, locating or spatially fixing the sensitizer, e.g. by dissolution, solubilization, adhesion or covalent binding. The "matrix" is typically an organic solvent or a polymer.

The sensitizer and the molecular oxygen must be in diffusion contact, (i.e. molecules of the sensitizer and oxygen molecules must be capable of colliding by diffusion of at least one of these molecular species) to ensure the ground state molecular oxygen quenching of the sensitizing excited states of the sensitizer. When this is the case, an energy transfer between the sensitizer and the molecular oxygen, i.e. a quenching, may occur, resulting in the sensitizing excited state of the sensitizer being deactivated to an electronic state of lower energy, most commonly the ground state, and singlet oxygen being formed.

The oxygen quenching processes of the sensitizing excited states have usually been observed to be diffusion-controlled. Hence, the actual values of the quenching rate constants depend on the viscosity of the matrix in which the sensitizer is present.

By excitation of a sensitizer, D, having a sensitizing excited state, D*(X), capable of producing a singlet oxygen, the generalized reaction scheme leading to singlet oxygen could be:

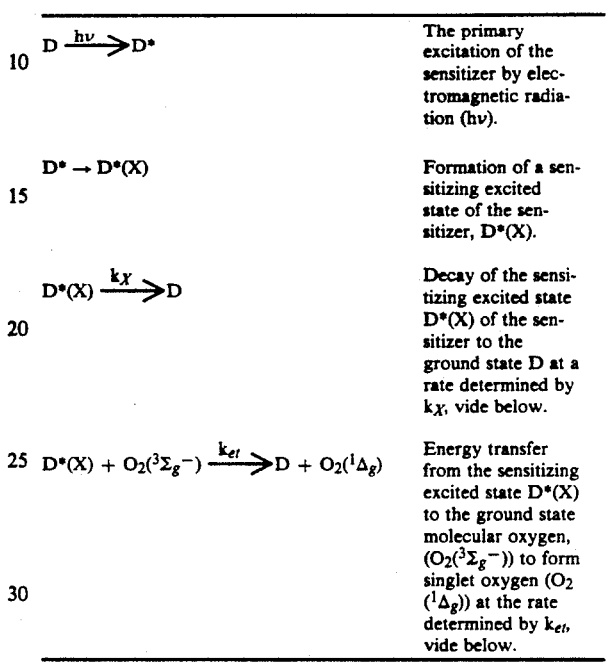

| | |
|---|---|
| $D \xrightarrow{h\nu} D^*$ | The primary excitation of the sensitizer by electromagnetic radiation ($h\nu$). |
| $D^* \rightarrow D^*(X)$ | Formation of a sensitizing excited state of the sensitizer, D*(X). |
| $D^*(X) \xrightarrow{k_X} D$ | Decay of the sensitizing excited state D*(X) of the sensitizer to the ground state D at a rate determined by $k_X$, vide below. |
| $D^*(X) + O_2(^3\Sigma_g^-) \xrightarrow{k_{et}} D + O_2(^1\Delta_g)$ | Energy transfer from the sensitizing excited state D*(X) to the ground state molecular oxygen, ($O_2(^3\Sigma_g^-)$) to form singlet oxygen ($O_2(^1\Delta_g)$) at the rate determined by $k_{et}$, vide below. |

The quantum yield (i.e. the number of molecules formed per absorbed photon) of singlet oxygen production $\phi(^1\Delta_g)$ wound be $$\phi(^1\Delta_g) = \phi_X \cdot \phi_{et}$$

wherein $\phi_X$ = the quantum yield of the formation of the sensitizing excited state, D*(X), $$\phi_{et} = \frac{k_{et}[O_2]}{k_X + k_{et}[O_2]} \tag{1}$$

the quantum yield of singlet oxygen formation from D*(X), i.e. the fraction of D*(X) giving singlet oxygen, $k_{et}$ being the rate constant for energy transfer from sensitizer to ground state molecular oxygen, $k_X$ being the rate constant for decay of the sensitizing excited state $$\left( k_X = \frac{1}{\tau_X}, \right.$$

$\tau_X$ being the lifetime of the sensitizing excited state), [$O_2$] being the concentration of molecular oxygen in the matrix containing the sensitizer.

The total yield $\phi_L(^1\Delta_g)$ of singlet oxygen luminescence (the number of photons emitted per photon absorbed) at 1270 nm will be given by $$\phi_L(^1\Delta_g) = \phi_P(^1\Delta_g) \cdot \phi_X \cdot \phi_{et}$$

wherein $\phi_P(^1\Delta_g)$ is the intrinsic phosphorescence quantum yield of singlet oxygen (i.e. the number of photons emitted per singlet oxygen molecule) under the actual conditions. Provided that $\phi_P(^1\Delta_g)$ and $\phi_X$ are independent of the oxygen concentration, the oxygen concentration dependence of the 1270-nm luminescence is determined solely by $\phi_{et}$. The assumption that $\phi_P(^1\Delta_g)$ and $\phi_X$ are independent of the oxygen concentration is probably only strictly valid for $\phi_P(^1\Delta_g)$, for which no evidence of oxygen concentration dependence can be found in the literature. The question whether $\phi_X$ will have any oxygen concentration dependence is determined by the chemical composition of the actual sensitizer system. For many potential sensitizers, $\phi_X$ will be the quantum yield of triplet formation $\phi_T$ (i.e. intersystem crossing from the singlet to the triplet manifold). In such cases, $\phi_X$ is likely to be dependent on the oxygen concentration, as oxygen-enhanced intersystem crossing is a common mechanism for singlet state quenching by oxygen. This process has actually been observed when tetraphenylporphyrin (H$_2$TPP) is used as a sensitizer (cf. Example 3).

As seen from equation (2) the total yield of singlet oxygen luminescence, $\phi_L(^1\Delta_g)$ is proportional to the intrinsic phosphorescence quantum yield of singlet oxygen, $\phi_P(^1\Delta_g)$. From the equation $$\phi_P(^1\Delta_g) = k_P(^1\Delta_g) \cdot \tau(^1\Delta_g)$$

where $k_P(^1\Delta_g)$ and $\tau(^1\Delta_g)$ are the radiative rate constant (number of photons emitted per unit of time) and lifetime of singlet oxygen respectively, it is seen that the 1270-nm luminescence yield will increase with increasing singlet oxygen lifetime provided that $k_P(^1\Delta_g)$ is matrix-independent. Experimentally, it has been found that in liquid phases $k_P(^1\Delta_g)$ is relatively independent of the type of matrix in question, whereas $\tau(^1\Delta_g)$ may change by at least a factor $10^3$ when the matrix is changed. The presence of OH-groups is known to be particularly effective in reducing $\tau(^1\Delta_g)$. Consequently, the preferred matrix should not contain OH-groups.

The oxygen dependence of the total singlet oxygen luminescence yield at 1270 nm, as given by the expression for $\phi_{et}$ (Equation 1), is determined by the three parameters $k_{et}$, $k_X$ and $[O_2]$, defined above. The main factors controlling the magnitude of these parameters are explained below:

$k_{et}$: The rate constant for energy transfer from sensitizer to ground state molecular oxygen. For essentially all potential sensitizers this process is diffusion-controlled. Hence, $k_{et}$ will be proportional to the sum of the diffusion constants of molecular oxygen and sensitizer in the matrix concerned.

$[O_2]$: For a given ambient partial pressure of molecular oxygen the concentration of molecular oxygen in the matrix (i.e. the matrix containing the sensitizer) will be proportional to the solubility of the molecular oxygen in the matrix concerned.

$k_X$: The rate constant for decay of the sensitizing excited state (in the absence of oxygen) is largely determined by the choice of sensitizer. Smaller effects of matrix and concentration of sensitizer may occur.

When combining equations (1) and (2) above and assuming that $\phi_P(^1\Delta_g)$ and $\phi_X$ are independent of the oxygen concentration it is seen that the total yield of singlet oxygen luminescence can be expressed as:

$$\phi_L(^1\Delta_g) = \phi_{max}\frac{k_{et}[O_2]}{k_X + k_{et}[O_2]} \quad (3)$$

$\phi_L(^1\Delta_g)$ being the total yield of singlet oxygen luminescence at 1270 nm obtained at oxygen concentration $[O_2]$, $\phi_{max}$ being the maximum yield of singlet oxygen luminescence obtainable in the system in question.

From equation (3) it can be seen that a plot of the singlet oxygen luminescence at 1270 nm, $\phi_L(^1\Delta_g)$, vs. $[O_2]$ will be a curve approaching asymptotically the maximum luminescence yield, $\phi_{max}$.

Under conditions where $k_{et}[O_2] >> k_X$ the value of $\phi_{et}$ will approach unity and the singlet oxygen luminescence will approach its maximum value, i.e. the luminescence intensity will be essentially constant with varying oxygen concentrations. The oxygen concentration in the matrix corresponding to a luminescence intensity of half the maximum value (i.e. $\phi_{et}=0.5$) will be given by $$[O_2]_{\frac{1}{2}} = k_X/k_{et}$$

or, expressed differently, half the maximum luminescence intensity will be obtained when the equality $$k_{et}[O_2] = k_X$$

is fulfilled. When $k_{et}[O_2] << k_X$, the luminescence intensity will be very small.

At moderate differences between $k_{et}[O_2]$ and $k_X$, the $\phi_L(^1\Delta_g)$ vs. $[O_2]$ curve will show a useful shape within an oxygen concentration range around and including $[O_2]_{\frac{1}{2}}$. Thus, for each individual system, there is an oxygen concentration range in which the size variation of $\phi_L(^1\Delta_g)$ (the total yield of singlet oxygen luminescence at 1270 nm) with the oxygen concentration (the slope of the curve) will be sufficient for utilization of the 1270-nm luminescence for oxygen concentration determination. Evidently, the term "sufficient" in this context is related to the luminescence detecting system used; with a more sensitive system, even small variations can be determined with sufficient accuracy, where as a less sensitive detection system will require a larger luminescence variation in order to secure a useful determination.

On combining equations (3) and (4) it appears that the total 1270 nm luminescence yield may be expressed as $$\phi_L(^1\Delta_g)/\phi_{max} = \frac{[O_2]/[O_2]_{\frac{1}{2}}}{1 + [O_2]/[O_2]_{\frac{1}{2}}}$$

which is equivalent to the function of $$y = \frac{x}{1 + x}$$

This function is illustrated in FIG. 7.

It will be seen that the luminescence $\phi_L(^1\Delta_g)$ approaches $\phi_{max}$ asymptotically when the oxygen concentration $[O_2]$ increases. As mentioned above, there is no particular limit at which the slope of the curve becomes so small that it is no longer useful for oxygen concentration determination—this depends on the detection system employed. However, for most practical applications, the system should be so adapted that the maximum oxygen concentration to be measured using the system corresponds to a $\phi_L(^1\Delta_g)$ of at the most 98% of $\phi_{max}$, often preferably a $\phi_L(^1\Delta_g)$ of at the most 95% of $\phi_{max}$, and most preferably a $\phi_L(^1\Delta_g)$ of at the most 90% of $\phi_{max}$. In accordance with this, the maximum oxygen concentration to be measured should result in a matrix oxygen concentration of at the most $50\bullet[O_2]_{\frac{1}{2}}$, preferably at the most $20\bullet[O_2]_{\frac{1}{2}}$ and most preferably at the most $10\bullet[O_2]_{\frac{1}{2}}$. In the following, it will be explained how the system can be adapted to the oxygen concentration range to be measured.

DETAILED DISCLOSURE OF THE INVENTION

The "1270-nm luminescence characteristics" as used herein refer to any way of characterizing or measuring the 1270-nm luminescence. Conventionally, the 1270-nm luminescence is characterized by the 1270-nm luminescence intensity, which is to be understood in its broadest sense, i.e. the magnitude of the 1270-nm luminescence signal obtained during continuous excitation or, the integrated value of the time-dependent 1270-nm luminescence signal obtained upon pulsed excitation or the first derivative of the decaying part of said time-dependent luminescence signal. However, also other ways of expressing the luminescence characteristics such as the amplitude and phase shift between the 1270-nm luminescence signal and a modulated oxygen excitation means are to be considered to be within the definition of the term "luminescence characteristics". Preferably, the 1270-nm luminescence intensity obtained during continuous excitation is measured.

The oxygen which is determined by the method according to the invention is molecular oxygen, i.e. $O_2$. As discussed above, the method of the present invention is based on the excitation of the oxygen molecules from the electronic ground state to an excited electronic state, the $^1\Delta_g$-state. Oxygen molecules in the $^1\Delta_g$-state are hereinafter and in accordance with conventionally used terms designated singlet oxygen or singlet molecular oxygen, and the $^1\Delta_g$-state of the oxygen molecules is referred to as the excited singlet state of molecular oxygen. These electronic states are defined by M. Kasha in "Singlet $O_2$", Vol. I, A. A. Frimer Ed., CRC-Press, Boca Raton, 1985, pp. 1–11.

In the method of the present invention, the radiative deactivation of singlet oxygen is utilized for determining the concentration of molecular oxygen. The radiative deactivation corresponds to an emission of light with a wavelength of about 1270 nm. In the gas phase the radiative deactivation of singlet oxygen corresponds to the emission of light with a wavelength of 1268.7 nm (M. Kasha, supra). In a condensed phase, the wavelength of the light originating from singlet oxygen is known less accurately but is usually quoted as 1270 nm. A typical emission spectrum of singlet oxygen in perfluorohexane is shown in FIG. 6. The full-width-at-half-maximum (FWHM) of the 1270-nm emission spectrum is typically about 30 nm. In relation to the present method, the width of the acceptable wavelength range in which the detection is performed may depend on the desired accuracy of the determination, the size of the background signal, etc. Normally, an acceptable luminescence signal of singlet oxygen is obtained when detecting within a wavelength range of 1270±90 nm, in particular 1270±60 nm, preferably 1270±40 nm, and the term "1270-nm luminescence characteristic" as used herein is intended to include luminescence measured at a wavelength range around 1270 nm, such as at the wavelength ranges stated above.

As mentioned above, it is known within the art that the 1270-nm luminescence is highly specific for the excited singlet state of molecular oxygen (M. Kasha, supra). Thus, in most cases there will be no need to take into account the part of the luminescence which originates from other components, as the magnitude of this part has usually been found to be negligible. Also, the noise attributable to the equipment used is usually insignificant compared to the singlet oxygen luminescence signal. In certain cases, however, it may be desirable to obtain a value of the luminescence characteristic which is solely attributable to the oxygen content of the sample. In these cases, it may be necessary to correct for the background signal derived from other components as well as for the equipment-derived noise. The term "measuring the 1270-nm luminescence characteristic" is therefore intended to include measuring the total 1270-nm luminescence characteristic which is optionally accompanied with or followed by a correction for the noise and background signal caused by the light emission from other components present in the sample.

In most cases, the amount of oxygen which is measured in the present method is stated as a concentration, e.g. as moles per liter or as a partial pressure, e.g. as mmHg or kPa, or equivalents thereto. As the unit of the oxygen content is dependent on the unit of the reference which is used to correlate the 1270-nm luminescence intensity with the actual oxygen concentration, this may be stated in another way. Thus as used herein, the term "concentration of molecular oxygen" is intended to mean the content of molecular oxygen stated in any convenient manner.

The 1270-nm luminescence signal obtained with the sample containing the oxygen to be measured is correlated with standard values based on 1270-nm luminescence signals obtained with reference samples of known oxygen content using the same or an equivalent system so as to quantify the unknown oxygen content.

As discussed above, singlet oxygen cannot be formed with any significant efficiency by direct absorption of electromagnetic radiation, and the oxygen molecules must be excited in another way. Conveniently, excitation of the oxygen molecules is performed by means of a sensitizing agent which has an excited electronic state (sensitizing excited state) capable of exciting molecular oxygen from the electronic ground state to the excited singlet state, the sensitizing agent being in diffusion contact with the sample.

The sensitizing agent is it is used herein may, in addition to the sensitizer discussed in the Theoretical Background section above, comprise a quencher capable of reducing the sensitizing excited state lifetime of the sensitizer. This will be discussed in detail below. In accordance with what has been explained above, the sensitizing agent is preferably embedded in a matrix in oxygen-diffusion contact with the sample. Alternatively, the sensitizing agent may be embedded in the sample.

The contact between the sensitizing agent and the molecular oxygen in the sample (which may be a fluid, i.e. a gas or a liquid, or a solid) is established through diffusion. As explained above, oxygen diffusion contact between the sample and the sensitizing agent is required, as oxygen molecules and the excited sensitizing agent must collide to permit the excitation of the oxygen molecules from the ground state to the excited singlet state.

In accordance with this, both the sample containing the molecular oxygen to be determined and the matrix, if used, must allow oxygen molecules to diffuse therein.

Singlet oxygen can be produced by quenching excited singlet states of the sensitizing agent as well as excited triplet states of the sensitizing agent. Excited triplet states are usually considered to be more efficient for singlet oxygen production than excited singlet states. In both cases, however, the sensitizing agent must have an energy gap of at least 0.98 eV between the starting electronic states and the final electronic states resulting from the molecular oxygen quenching, as the energy transferred to the molecular oxygen must be of a magnitude of at least 0.98 eV (the energy of the excited singlet state of oxygen).

Certain sensitizing agents, e.g. certain porphyrins, are capable of converting molecular oxygen to superoxide (i.e. $O_2^-$, the radical anion of oxygen) by an electron transfer mechanism through illumination. Superoxide, which is fairly stable in non-polar organic solvents, is known to be an efficient quencher of singlet oxygen (Guiraud, H. J. and Foote, C. S., *J. Am. Chem. Soc.* 98, 1984 (1976). When superoxide is formed in a singlet oxygen-containing sample, it may quench part of the singlet oxygen resulting in a 1270-nm luminescence intensity which is too low in relation to the equivalent of the true molecular oxygen concentration of the sample. Due to the stability of superoxide in organic solvents, even a very slow formation of superoxide may be critical in these solvents, as a significant superoxide concentration may be built up eventually. The sensitizing agent is therefore preferably a substance having an oxidation potential of the sensitizing excited state which essentially renders the sensitizing agent incapable of converting molecular oxygen to superoxide. Thus, the oxidation potential of the sensitizing agent in the sensitizing excited state must be higher than the reduction potential of oxygen in the matrix in question.

Accordingly, the reduction potential of oxygen in the matrix would be valuable as a guideline for the choice of matrix and sensitizing agent, but this quantity is only known in very few solvents. In acetonitrile, the reduction potential of oxygen has been reported as −0.82 V vs. saturated calomel electrode (SCE). It is likely that the reduction potential of oxygen will tend to be lower than −0.82 V (vs. SCE) in matrices less polar than acetonitrile and for practical purposes a sensitizing agent having an oxidation potential of the sensitizing excited state higher than −0.7 V (vs. SCE) will be considered to be useful.

An example of the adverse effect of superoxide formation is a reduction of the 1270-nm luminescence signals observed for aerated samples of zinc-octaethylporphyrin (ZnOEP) and zinc-tetraphenylporphyrin (ZnTPP) (cf. Examples 1a and 2a and FIGS. 8 and 9, respectively). In accordance with the theoretical explanation above, these substances have oxidation potentials of their sensitizing excited states which are lower than the estimated reduction potential of oxygen in toluene. The triplet state oxidation potentials of ZnOEP and ZnTPP are −1.13 V vs. SCE and −0.88 V vs. SCE, respectively. For samples containing tetraphenylporphyrin ($H_2$TPP) (cf. Example 3 and FIG. 10), no similar signal reduction was observed in accordance with the higher triplet state oxidation potential of $H_2$TPP (−0.48 V vs. SCE).

In accordance with what is described above, the system in which the method of the invention is performed should preferably be so adapted that the maximum oxygen concentration to be measured using the system corresponds to a $\phi_L(^1\Delta_g)$ of at the most 98% of $\phi_{max}$, often preferably a $\phi_L(^1\Delta_g)$ of at the most 95% of $\phi_{max}$, or most preferably a $\phi_L(^1\Delta_g)$ of at the most 90% of $\phi_{max}$. In the case where the sensitizing agent is embedded in a matrix, this means that the concentration of oxygen in the sample (the "ambient" concentration seen from the point of view of the sensitizing agent in the matrix) should be one which results in a concentration of oxygen in the matrix which gives a luminescence fulfilling the criteria stated above. The sensitizing agent/matrix system may be adjusted so that this condition is fulfilled for a particular range of ambient oxygen concentration by varying either side of equality (5). In the following, these two possibilities:

modifying the sensitizing excited state lifetimes, i.e. adjusting $k_X$, adjusting or modifying $k_{et}[O_2]$ will be discussed separately.

Adjusting $k_X$

The lifetimes $1/k_X$ of the sensitizing excited states may be modified by adding a quencher which deactivates the sensitizing excited state, preferably without affecting the primary yield of that state. Thus, as mentioned above, the sensitizing agent may comprise a sensitizer having an excited state capable of exciting molecular oxygen from the electronic ground state to the excited singlet state and a quencher capable of deactivating the sensitizing excited state of the sensitizer so as to reduce the sensitizing excited state lifetime of the sensitizer, the quencher being in contact with the sensitizer. The quencher can deactivate the sensitizing excited state through energy transfer or electron transfer mechanisms. In the presence of a quencher (Q), the modified lifetime of the sensitizing excited state ($\tau_X'$) will be determined by

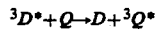

$$1/\tau_X' = (1/\tau_X) + k_Q[Q]$$

where $1/\tau_X = k_X$ and $k_Q$ is the rate constant for quenching of the sensitizing excited state by Q.

When the sensitizing excited state is the excited triplet state of the sensitizer, energy transfer quenching corresponds to the following reaction:

$$^3D^* + Q \rightarrow D + {^3Q^*}$$

where D and Q represent an electronic state of lower energy of the sensitizer and the quencher, respectively, and $^3D^*$ and $^3Q^*$ represent the excited triplet states of the sensitizer and the quencher, respectively. This process will generally be effective if $E_T(D) > E_T(Q)$, $E_T(D)$ and $E_T(Q)$ being the triplet energies of sensitizer and quencher. The modification of the triplet lifetime of ZnOEP by energy transfer to tetraphenylbutadiene (TPB) is illustrated in Example 1b.

Electron transfer quenching of an excited triplet state is based on the following reactions:

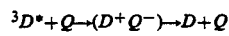

$$^3D^* + Q \rightarrow (D^+ Q^-) \rightarrow D + Q$$

or

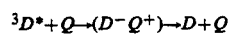

$$^3D^* + Q \rightarrow (D^- Q^+) \rightarrow D + Q$$

where $(D^+ \; Q^-)$ and $(D^- \; Q^+)$ are the geminate ion pairs formed by electron transfer from or to the sensitizer triplet state. Electron transfer will be a spontaneous process when $E_{ox} - E_{red} - E_T(D) < 0$, $E_{ox}$ and $E_{red}$ being the reversible one-electron oxidation and reduction potentials of the electron donor and electron acceptor, respectively. As described in Examples 1C and 2b and 2c, electron transfer quenching of the triplet states of ZnOEP and ZnTPP by duroquinone (DQ) results in oxygen sensitivities which depend upon the amount of DQ added.

A general problem with electron transfer quenching of excited triplet states is interference from quenching of the excited singlet state. Electron transfer reactions which are exothermic for the excited triplet state will be even more exothermic with the excited singlet state as the inequality $E_S(D) > E_T(D)$ is always obeyed for all practical purposes, $E_S(D)$ being the singlet energy of the sensitizer. Quenching of the excited singlet state will result in a reduced yield of the triplet state and hence in a reduced 1270-nm luminescence intensity. The situation in which the quencher solely deactivates the excited singlet state and not the triplet state may also arise. This problem has been encountered in attempting to modify the triplet lifetime of H₂TPP by using benzoquinone as a quencher (cf. Example 3 and FIG. 10). The most effective way to minimize singlet quenching interference will be to choose sensitizers with very short singlet lifetimes, preferably below 2 ns. Tetraphenylporphyrins (H₂TPP's) substituted with bromine in the phenyl groups, as disclosed e.g. in Quimby, D. J. and Longo, F. R., *J. Am. Chem. Soc.* 97, 1975, p. 5111 and in Kim, J. B., Leonard, J. J. and Longo, F. R., *J. Am. Chem. Soc.* 94, 1972, p. 3986, may prove valuable in this respect. They are effective sensitizers of singlet oxygen and they have reportedly singlet lifetimes which are considerably below 1 ns.

Adjusting $k_{et}[O_2]$

As mentioned above in connection with equations (1) and (2), the oxygen quenching rate constant $k_{et}$ is proportional to the diffusion constant of molecular oxygen in the matrix in question and the concentration of molecular oxygen ($[O_2]$) in the matrix is equal to the product of the solubility of molecular oxygen in the matrix and the ambient partial pressure of oxygen. The quantity, $k_{et}[O_2]$ shown in equation (2) will therefore be proportional to the permeability (the product of the diffusion constant and the solubility of molecular oxygen) of the matrix for molecular oxygen. The influence of the matrix on the lifetime of the sensitizing agent, i.e. $1/k_X$, is usually negligible. Consequently, the oxygen sensitivity of a given sensitizing agent may be adjusted to the desired range of oxygen concentrations by selecting a matrix with an appropriate oxygen permeability. Permeabilities of polymers for oxygen are tabulated in the literature and these tables will be valuable guidelines in the choice of a suitable matrix. In Example 4, the $[O_2]_{\frac{1}{2}}$ values for various combinations of sensitizing agents and matrices are stated.

When choosing between two matrices with equal permeability for oxygen, the one with the lowest oxygen solubility (and hence the highest diffusion constant) should be preferred, as this will give the fastest response to changes in oxygen concentrations. In case of competition between singlet oxygen production and the above-discussed superoxide production, the production of singlet oxygen will be favoured in a non-polar matrix.

According to the present invention, the sensitizing excited state of the sensitizing agent is formed from another electronic state, in most cases the electronic ground state of the sensitizing agent, by absorption of electromagnetic radiation. Preferably, the wavelength of electromagnetic radiation is less than 1270 nm, more preferably in the range of 300–1000 nm. The wavelength of the electromagnetic radiation will conveniently be chosen so as to match a region of strong absorption by the sensitizing agent in question. Thus, the radiation source may be filtered by one or more filters to filter off light of an undesirable wavelength. Examples of useful filters are filters which remove infrared radiation, e.g. a 2 mm KG5 filter (from Schott Glaswerke, West Germany) or filters which minimize the direct excitation of the quencher in question, e.g. a 2 mm GG385 filter (from Schott).

The electromagnetic radiation of the sensitizing agent may take place from any convenient radiation source. The light derived from the electromagnetic radiation source may be coherent or incoherent and may be continuous, modulated or pulsed. A pulsed excitation source may prove valuable, as it will allow the time-dependence of the 1270-nm luminescence intensity to be recorded. Kinetic analysis of the time-dependence can give separate information about singlet oxygen producing and depleting processes. Potential interfering substances (i.e. substances other than oxygen which affect the 1270-nm luminescence signal) may either act as quenchers of the sensitizing excited state (i.e. decrease the yield but increase the apparent rate of singlet oxygen production) or of singlet oxygen (i.e. increase the rate of singlet oxygen decay) and these mechanisms may be distinguished by kinetic analysis of the time-resolved 1270-nm luminescence. In IUPAC Commission of Photo Chemistry, "Glossary of terms used in photochemistry", Parts 1, 2 and 3, *EPA Newsletter*, November 1985, March 1986 and July 1986, respectively, different light sources which are useful in the present method are mentioned. Among these are laser diodes, gas lasers such as argon ion, cadmium-neon, CO₂, helium-neon, and a nitrogen laser or solid state lasers such as a niodymium (YAG or glass) or a ruby laser and dye lasers. Also conventional light-emitting diodes, flash lights or discharge lamps and high pressure mercury lamps, medium pressure mercury lamps, low pressure mercury lamps and antimony-xenon, mercury-xenon, quartz-iodine, tungsten-halogen, resonance and xenon lamps will be useful. This list should not be considered as exhaustive as any source of electromagnetic radiation of a suitable wavelength range may be utilized.

The 1270-nm luminescence is measured by a detector having a sufficient sensitivity around 1270 nm. Conveniently, the luminescence is filtered by one or more filters which are employed to filter out light of irrelevant wavelengths so as to ensure that only light of the desired wavelength (around 1270 nm) reaches the detector. Preferably, the filter is an interference filter, e.g. a BP-1270-080-B filter manufactured by Spectrogon, New Jersey, U.S.A. The detector may be a photomultiplier tube (PMT) or a solid state detector such as a diode made from indium gallium arsenide (InGaAs), lead sulphide (PbS) or germanium (Ge). Preferably, the detector is an InGaAs detector, e.g. of the type FID 13S13WX obtainable from Fujistu Microelectronics, Inc., California.

Preferred sensitizing agents to be used in the present invention are compounds having i) high-stability towards photo-decomposition (including photooxidation) and ii) large optical extinction coefficients. Photochemical stability is desirable in order to produce a singlet oxygen measuring system capable of long-term functioning during continuous illumination. A large optical extinction coefficient is desirable to obtain a large optical density with a short optical path length, i.e. a thin layer of matrix which in turn will give a measuring system with a fast response to changes in oxygen concentrations. A lower optical extinction coefficient of the sensitizer may of course be compensated for by applying a higher sensitizer concentration. However, for most practical purposes, especially in connection with polymer matrices, a sensitizer concentration approaching the maximum amount dissolvable in the matrix, will be employed.

Generally, useful classes of sensitizers are porphyrin and porphyrin-related compounds such as metal-free porphyrin, metallo-porphyrins, phtalocyanins, metallo-phtalocyanins and derivatives thereof. Examples of useful porphyrins include octaalkylporphyrins, tetraphenylporphyrin, tetrabenzoporphyrin and substituted derivatives thereof. In particular, fluorinated (partially or wholly) derivatives are useful because of their stability towards photooxidation. Furthermore, it has been found that the Zn(II)-complex of tetrabenzoporphyrin ($H_2$-TBP) has an extinction coefficient close to $10^5 M^{-1} cm^{-1}$ at the wavelength of a He-Ne-laser. This compound (ZnTBP), but also other metallo-complexes of $H_2$TBP as well as fluoro-, chloro-, bromo-, alkyl- and aryl- such as phenyl-substituted derivatives must therefore be considered very attractive candidates for use as singlet oxygen sensitizers. Further, tetrabenzoporphyrins substituted with tert-butyl-groups and meso-(tetraaryl)-tetrabenzoporphyrins which are easily synthesized have favourable solubility properties. The porphyrins and in particular their metallo-complexes may therefore be useful as singlet oxygen sensitizers.

When the 1270-nm luminescence intensity is used to quantify the concentration of oxygen, the measured signal (i.e. the intensity) will be directly proportional to the absorbed intensity of the excitation light source. Therefore, it is desirable to be able to correct the measured signal for variations in the intensity of the excitation light source or in the efficiency of light absorption by the sensitizing agent system, e.g. in connection with bleaching of the sensitizing agent. This can be accomplished by using a sensitizing agent which fulfills the following criteria:

1) It has fluorescence.
2) The fluorescence is well separated from 1270 nm.
3) The fluorescence has a lifetime which is sufficiently short to make the fluorescence quantum yield independent of oxygen.

With a sensitizing agent having the above-stated properties, the fluorescence intensity of the sensitizing agent measured simultaneously with the measurement of the 1270-nm luminescence may give a signal by which the 1270-nm luminescence signal can be corrected.

Metallo-porphyrins have typically fluorescence lifetimes which are <3 ns. Consequently, the fluorescence quantum yields of these compounds will be essentially independent of oxygen even in liquid matrices. Substitution of Br into the phenyl groups of $H_2$TPP reduces the fluorescence lifetime considerably, so these compounds may also be useful in this respect. The free base porphyrins (e.g. $H_2$OEP, $H_2$TPP and $H_2$TFPP) typically have fluorescence lifetimes of 10–15 ns. In liquid matrices, these compounds will have oxygen-dependent fluorescence quantum yields. However, the use of matrices with low oxygen permeabilities (e.g. polymers) will reduce the fluorescence quenching by oxygen. Therefore, intensity correction by sensitizing agent fluorescence should be possible with all fluorescing porphyrins when matrices of low oxygen permeability are used.

Among the porphyrin-related compounds a new class of synthetic compounds which are structural isomers of porphyrins, i.e. the porphycenes, are useful. This class is described by E. Vogel et al. (*Angew. Chem.* 98, 1986, p.262) and these compounds are reportedly very stable towards photooxidation.

Other metallo-porphyrins and metallo-phtalocyanins than the above-mentioned ZnTBP include complexes of metals selected among Zn(II), Pd(II), Pt(II), Ru(II), and Os(II).

Other potentially useful sensitizers are tris α-diimine complexes of transition metals such as Ru(II), Os(II), Ir(III) and Rh(III), as described by e.g. Bacon and Demas in UK Patent Application No. 2,132,348 A.

A variety of dyes such as rose bengal, erythrosin, eosin, fluorescein, and methylene blue may also be useful.

Polycyclic aromatic compounds such as pyrene, naphthalene, anthracene, or decacyclene, or derivatives thereof are potential sensitizers.

As mentioned above, the reduction of the sensitizing excited state lifetime of the sensitizing agent may take place by different mechanisms. The sensitizing excited state lifetime of the sensitizing agent may be reduced by intermolecular quenching such as by energy transfer process, which is preferably an exothermic process. An example of a quencher which deactivates the sensitizing excited state of the sensitizing agent by this type of process is a substituted polyene, e.g. tetraphenylbutadiene.

The intermolecular quenching may also involve an electron transfer process, which is preferably an exothermic electron transfer process. Electron acceptors which are capable of oxidizing the sensitizing excited state of the sensitizing agent are quinones such as benzoquinone or duroquinone or substituted quinones, preferably halogen-substituted quinones. The intermolecular quenching by an electron transfer process may, however, also take place when the quencher is an electron donor capable of reducing the sensitizing excited state of the sensitizing agent.

As will be understood from the above discussion, the diffusion contact between the sensitizing agent and the sample may be established by simply adding the sensitizing agent to the sample containing the molecular oxygen and dissolving the sensitizing agent in the sample, or it may be established by contacting the sample with a matrix in which the sensitizing agent is embedded. If desired, an oxygen-permeable membrane may be inserted between the sample and the matrix containing the sensitizing agent. In particular in connection with measurements on samples of biological origin, a membrane separation may be useful in order to avoid possible interference from compounds other than oxygen and may also be useful for long-term continuous monitoring of the oxygen concentration of a flowing sample, e.g. in vivo monitoring of blood oxygen concentration.

Of course, if the sensitizing agent per se has physical/chemical properties which permit its use without it being embedded in a matrix, and without being dissolved in the sample, this is also within the scope of the present invention.

As discussed above, the presence of OH-groups in the matrix in which the sensitizing agent is embedded should preferably be avoided, as these OH-groups are very effective for reducing the lifetime of the singlet oxygen. As the singlet oxygen lifetime is critical to the measurements as discussed above, useful matrices may be selected using the singlet oxygen lifetime in the matrix in question as a guideline.

Preferably, the matrix comprises an organic solvent or a polymer. Examples of potentially suitable organic solvents are aromatic solvents such as benzene, toluene, xylene, and similar compounds. Other examples of potentially useful solvents are acetone, acetonitrile and halogenated solvents such as halogenated aromatic solvents, e.g. chlorobenzene, bromobenzene and hexafluorobenzene, and methylenechloride, chloroform, carbontetrachloride, chlorofluorocarbons, e.g. CF11, CF113, and tetrachloroethylene.

Examples of potentially useful polymers are polyvinylchloride (PVC) and plasticized PVC, polycarbonate silicone copolymers, silicone rubbers, polymethylmethacrylate (PMMA), polytetrafluoroethylene (PTFE), cellulose acetate, polystryene and polyurethane.

The above-stated examples of useful matrix components are only intended as a guideline and should not be considered to be an exhaustive list.

The oxygen-containing samples to be analyzed are preferably liquid samples of biological origin, such as blood, having a molecular oxygen concentration which is at a physiological level corresponding to oxygen partial pressures in the range of from zero or just above zero, i.e. a few mmHg, to several hundred mmHg, i.e. about 800 mmHg, preferably up to 400 mmHg, more preferably up to 150 mmHg, most preferably up to 120 mmHg. Thus, sensitizing agent/matrix combinations which allow determination of oxygen partial pressures varying within the entire physiological range will be preferred. The preferred sensitizing agent/matrix combinations for determination of physiological oxygen partial pressures are those combinations which show $[O_2]_{\frac{1}{2}}$ values of from 10 to 200 mmHg, preferably from 20 to 150 mmH, and in particular from 30 to 120 mmHg.

The oxygen-containing sample may also be an oxygen-containing has of biological origin. This will occur when applying the method according to the invention to transcutaneous measurement of oxygen or to measurement of respiration gases.

A suitable system for determining the concentration of molecular oxygen in a sample by the methods of the present invention may comprise means for exciting oxygen molecules of the sample from the electronic ground state to the excited $^1\Delta_g$ state (excited singlet state), means for measuring a 1270-nm luminescence characteristic of the excited oxygen molecules, and means for correlating said 1270-nm luminescence characteristic with the concentration of molecular oxygen in the sample. Preferably, the means for exciting oxygen molecules of the sample from the electronic ground state to the excited $^1\Delta g$ state (excited singlet state) comprise an electromagnetic radiation source, preferably one wherein the electromagnetic radiation is of a wavelength of less than 1270 nm, preferably in the range of 300–1000 nm, and a sensitizing agent, optionally embedded in a matrix, the sensitizing agent being in diffusion contact with the sample.

Preferably, the means for measuring a 1270-nm luminescence characteristic of the excited oxygen molecules comprise a detector, optionally covered by a filter and being capable of measuring a luminescence characteristic at a wavelength of about 1270 nm, the detector optionally being connected to an amplifier circuit.

The means for correlating the 1270-nm luminescence characteristic with the concentration of molecular oxygen in the sample may be any suitable signal and data processing and comparison means such as any combination of electronic converters or amplifiers and computer or microprocessor means, including data storage means for storing the standard luminescence/oxygen values with which the correlation is made. The means for correlating the 1270-nm luminescence characteristic with the concentration of molecular oxygen in the sample may also simply comprise a standard curve.

A suitable device for measuring the concentration of molecular oxygen in a sample, said device comprising a matrix in which a sensitizing agent is embedded, the matrix being arranged so as to allow the sensitizing agent to receive excitation radiation from an external electromagnetic radiation source thereby forming a sensitizing electronic state of the sensitizing agent; a region wherein the sample when under test will be in diffusion contact with the sensitizing agent so as to allow for excitation of oxygen molecules of the sample to the excited singlet state by the sensitizing agent in its sensitizing electronic state; a transmission path for transmitting radiation from the excited singlet state oxygen molecules towards 1270-nm luminescence measuring means. Preferably, the matrix in which the sensitizing agent is embedded is positioned on a support, e.g. a glass cover slip.

The region wherein the sample will be in diffusion contact with the sensitizing agent may be a surface part of the device according to the invention or may be a sample accommodating chamber defined in or at the device according to the invention.

For example, the sample accommodating chamber may be a cuvette provided with sample inlet means and sample outlet means as will normally be found in automated analyzers. Alternatively, the sample accommodating chamber may be a cuvette provided with sample inlet means only, as will normally be seen in disposable devices. Other configurations of the sample accommodating chamber will also be conceivable, e.g. the sample accommodating chamber may be an absorbing fibrous or porous structure arranged adjacent to the matrix or a structural part defined to the same extent by a body surface. The latter configuration is contemplated for devices adapted to non-invasive transcutaneous oxygen measurements.

In particular in connection with invasive in vivo oxygen measurements, the region wherein the sample when under test will be in diffusion contact with the sensitizing agent could well be a surface part of the device.

BRIEF DESCRIPTION OF THE DRAWINGS

The invention will now be further described with reference to the drawing, in which.

as described above.

Figure 8:
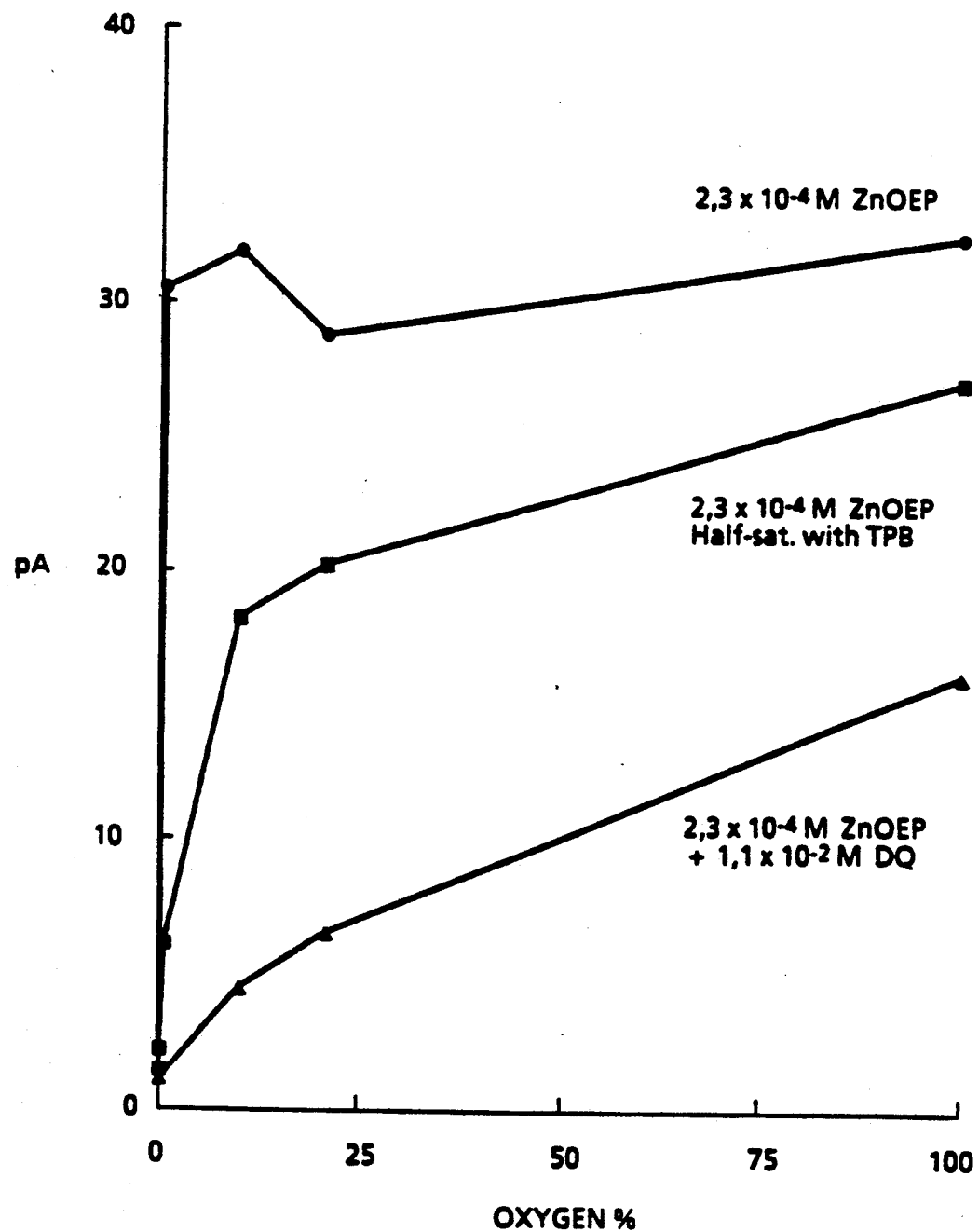
Figure 9:
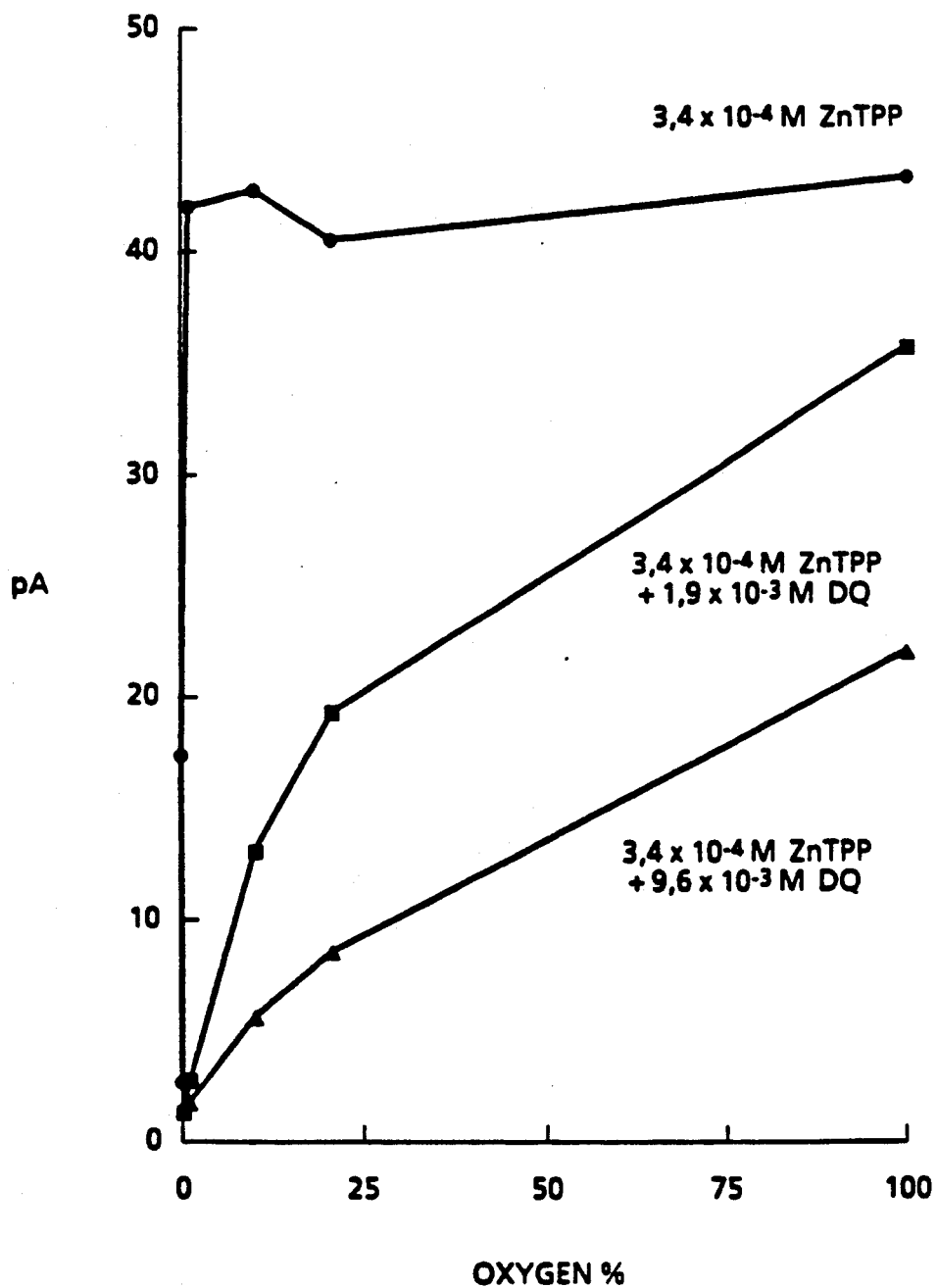
Figure 10:
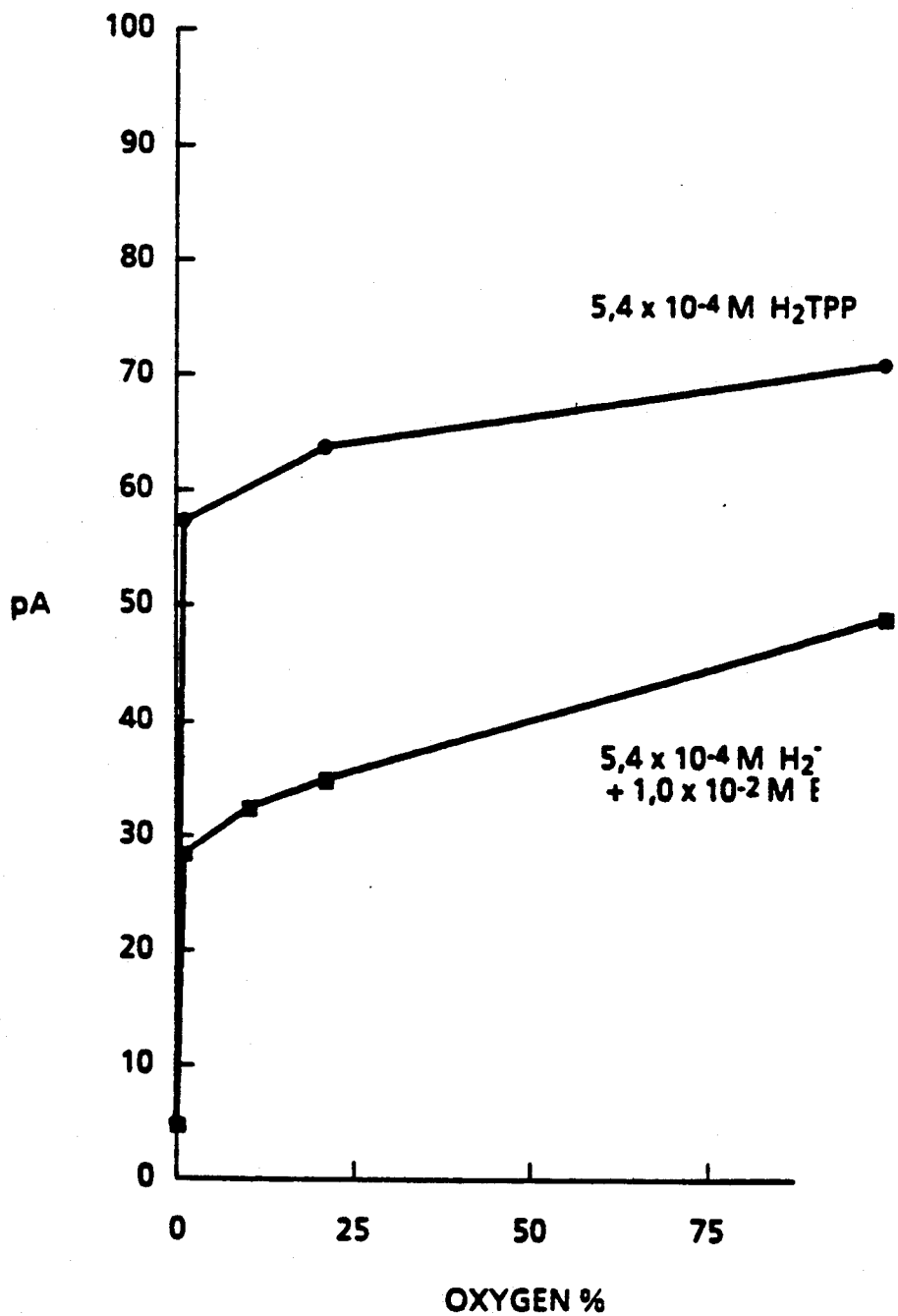

FIGS. 8, 9 and 10 are diagrammatical views illustrating results obtained in accordance with Examples 1-3 to be described below.

DETAILED DESCRIPTION OF THE DRAWINGS

Figure 1:
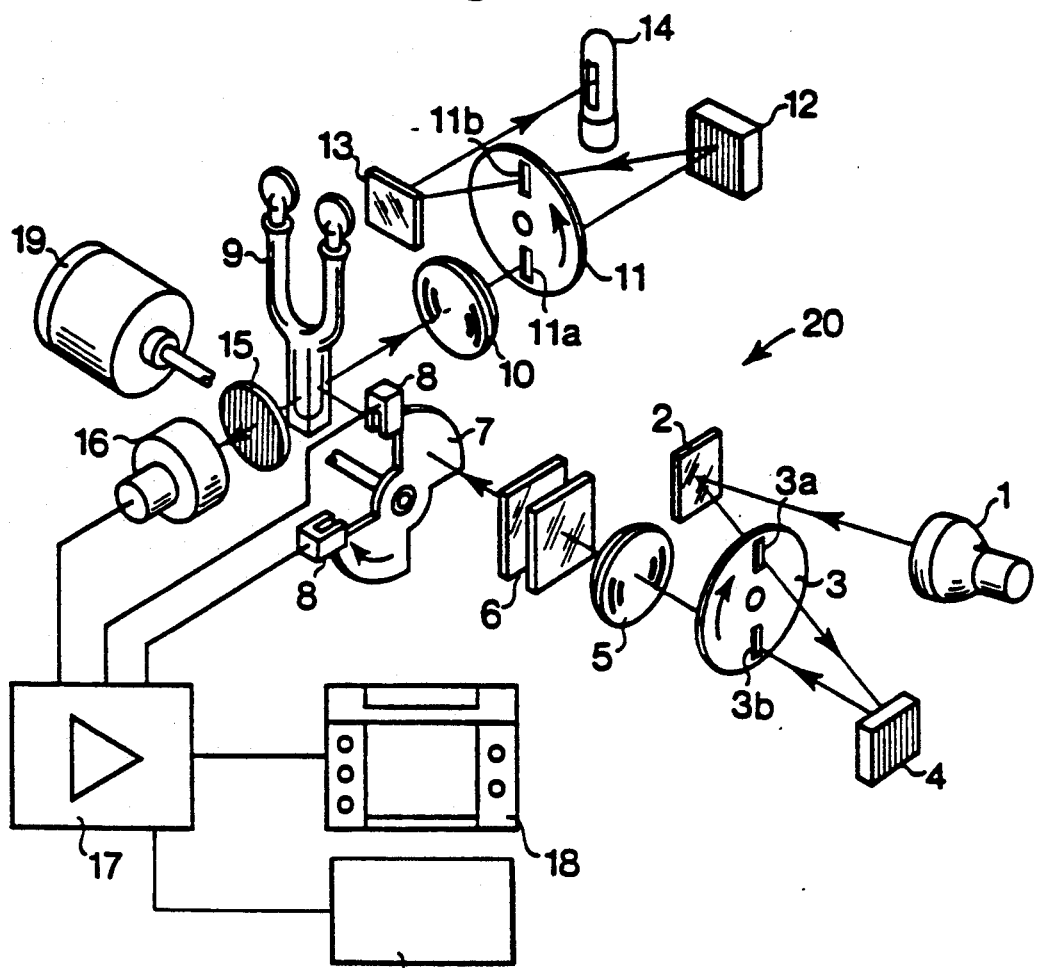
FIG. 1 is an overall diagrammatical and perspective view of a test bench or set-up embodiment of a system according to the present invention.

In FIG. 1 a test bench embodiment of a system according to the present invention is shown designated the reference numeral 20 in its entirety. The system 20 shown in FIG. 1 is employed in Examples 1-3 described below. An essential part of system 20 is a Shimadzu spectrofluorophotometer RF540 (obtainable from Shimadzu Corp., Kyoto, Japan). The Shimadzu RF540 comprises an excitation part, an emission part and a sample compartment part. In FIG. 1 components 1-5 are usual components of the excitation part of the Shimadzu RF540 and components 10-13 are the usual components of the emission part of Shimadzu RF540. Components 6-9 and 14-19 have been provided for the purpose of the present invention, components 6-9 and 15-16, 19 being located in the sample compartment part of Shimadzu RF540. The system 20 will now be described in further detail.

An excitation source 1 which includes a 150 W xenon arc, emits light, which is expanded by an ellipsoidal mirror of the excitation source 1. The light is passed to a concave mirror 2 and further to a concave diffraction grating 4 through a slit 3a of a first slit assembly 3 and back through a slit 3b of the first slit assembly 3. Together, the first slit assembly 3 and the diffraction grating 4 constitute a monochromator of an off-plane type. From the monochromator, the light is passed through a pair of light-collecting lenses 5. The collected light is then passed through a pair of filters 6, the first filter being a 2 mm KG5 (Schott) filter which filters out infrared radiation from the light, and the second filter being a 2 mm GG 385 (Schott) filter which filters out ultraviolet radiation. From the filters 6, The light passes through a chopper disc 7, adjacent to which two slotted optical switches OPB804 (from TRW Corporation, Texas, U.S.A.) 8 are arranged, which slotted optical switches are connected to two inputs of an amplifier circuit 17. The chopper disc 7 is rotated by means of an electromotor 19. The amplifier circuit 17 receives electrical signals from the slotted switches 8, which signals represent the presence or absence of the chopper disc 7 in the slots of the slotted switches 8. Due to the arrangement of the slotted switches 8 relative to the chopper disc 7 and the light beam these signals also represent light passing/not passing the chopper disc 7. A SUPRASIL fluorescence cell (Hellma) 9 containing the oxygen-containing sample is irradiated by the light which has passed the chopper 7. For control purposes, light emitted from the sample contained in the fluorescence cell 9 is passed through a light-collecting lens 10 of the same type as the lens 5. The light is then passed through a slit 11a of a second emission slit assembly 11 to a concave diffraction grating 12, through a slit 11b of the second slit assembly 11 to a concave mirror 13 and the signal is collected by a red sensitive photomultiplier 14 of the type R928 from Hamamatsu Photonics K.K., Japan. Together, the components 10-14 of the system 20 constitute a light emission control system serving the purpose of measuring the luminescence generated by the sensitizing agent, which luminescence is used to control the activity of the sensitizing agent. For measuring the 1270-nm luminescence of the sample, the luminescence of the sample contained in the fluoroescence cell 9 is passed through an interference filter 15 of the type BP-1270-080-B manufactured by Spectrogon having maximum transmission (73%) at 1265 nm and a full-width-at-half-maximum (FWHM) of 80 nm. The resulting luminescence is detected by an InGaAs diode 16, the diode being of the type Fujistu 13S13WX and contained in an aluminum container. The diode signal is transferred to a third input of the amplifier circuit 17 constituting a lock-in amplifier (10 mV/pA), which correlates the measuring signals received from the InGaAs diode 16 with the electrical signals received from the slotted switches 8 so as to obtain a luminescence signal which is the difference between the luminescence signals of the irradiated sample and the non-irradiated sample, respectively. The signal is transferred to a recorder 18 of the type Radiometer REC80.

Figure 2A:
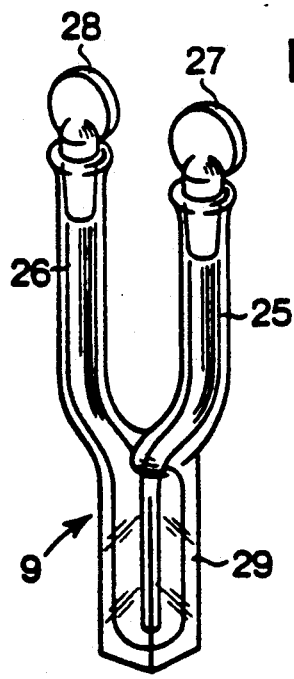
FIG. 2a is a perspective view of a first embodiment of a test cell constituting a component of the system shown in FIG. 1.

FIG. 2a illustrates in greater detail the SUPRASIL fluorescence cell 9 shown in FIG. 1, which cell contains the oxygen-containing sample to be measured. The fluorescence cell 9 is a modification of a Hellma standard fluorescence cell of the type 101QS* (5×5 mm), the standard cell constituting a bottom part 29 of the fluorescence cell 9. For the purpose of the present invention, the bottom part 29 has been provided with inlet and outlet tubes 25 and 26, respectively. Through the inlet tube 25, a solution of the sensitizing agent, i.e. a sensitizer optionally in admixture with a quencher, in an appropriate matrix, is supplied to the interior of the cell 9 in a sufficient amount so as to ensure that the solution fills the bottom part 29 and at least part of the outlet tube 26. The inlet and outlet tubes 25 and 26, respectively, are closed with glass stoppers 27 and 28, respectively. The gas containing the molecular oxygen to be measured is bubbled through the sensitizing agent containing solution through the inlet tube 25, while the glass stopper 28 is removed so as to avoid a build-up of pressure in the cell 9. After the solution containing the sensitizing agent has been saturated with gas, the glass stopper 28 is placed in the outlet tube 26 and subsequently the glass stopper 27 is placed in the inlet tube 25, after which the sample-containing cell is subjected to irradiation.

Figure 2B:
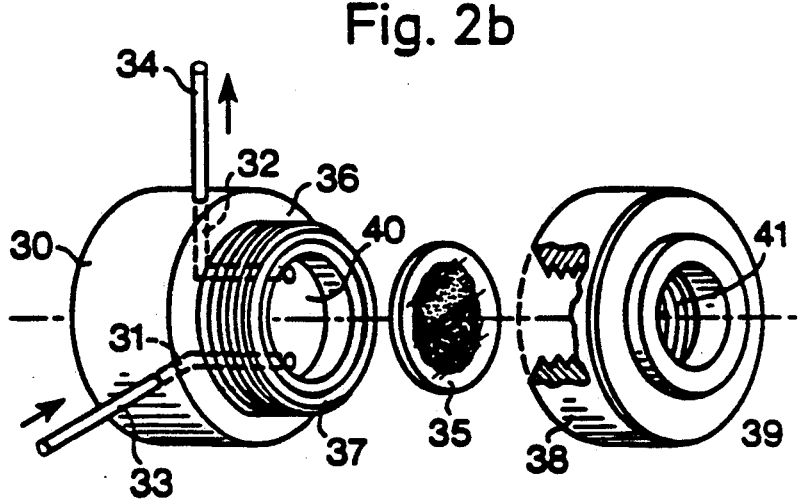
FIG. 2b is a perspective view of an alternative or second embodiment of a test cell.

FIG. 2b illustrates an alternative test cell which may used in a test bench corresponding to the test bench illustrated in FIG. 1. The test cell is arranged in a solid sample holder 204-26836-01 manufactured by Shimadzu Corp., Kyoto, Japan. A circular cylindrical body 30 is equipped with inner bores 31 and 32, respectively, which inner bores are connected to an inlet tube 33 and an outlet tube 34, respectively. The circular cylindrical body 30 is equipped with a protruding ring 36 having an outer or male thread and being equipped with an O-ring 37. A fixation ring 38 is equipped with an inner or female thread 39 matching the outer or male thread of the ring 36. A probe 35, being an HF-etched 19 mm diameter microscope glass slip (from Chance Propper Ltd., Wesley, England) on one of the surfaces of which a mixture of a matrix component and a sensitizing agent is cast, is placed between the circular cylindrical body 30 and the fixation ring 38 and then subjected to illumination through a through-hole 41 of the fixation ring 38. The oxygen-containing sample to be investigated is passed through the inlet tube 33 and further through the inner bore 31 so as to accommodate the space defined by a blind hole 40 of the circular cylindrical body 30 and the probe 35 resulting in diffusion contact between the sample and the probe 35. An equilibrium between the oxygen content of the oxygen-containing sample and the oxygen content of the matrix will be established. The sample is passed out of the test cell through the inner bore 32 and the outlet tube 34. The flow of the oxygen-containing sample passing the probe 35 may be continuous or intermittent.

Figure 3:
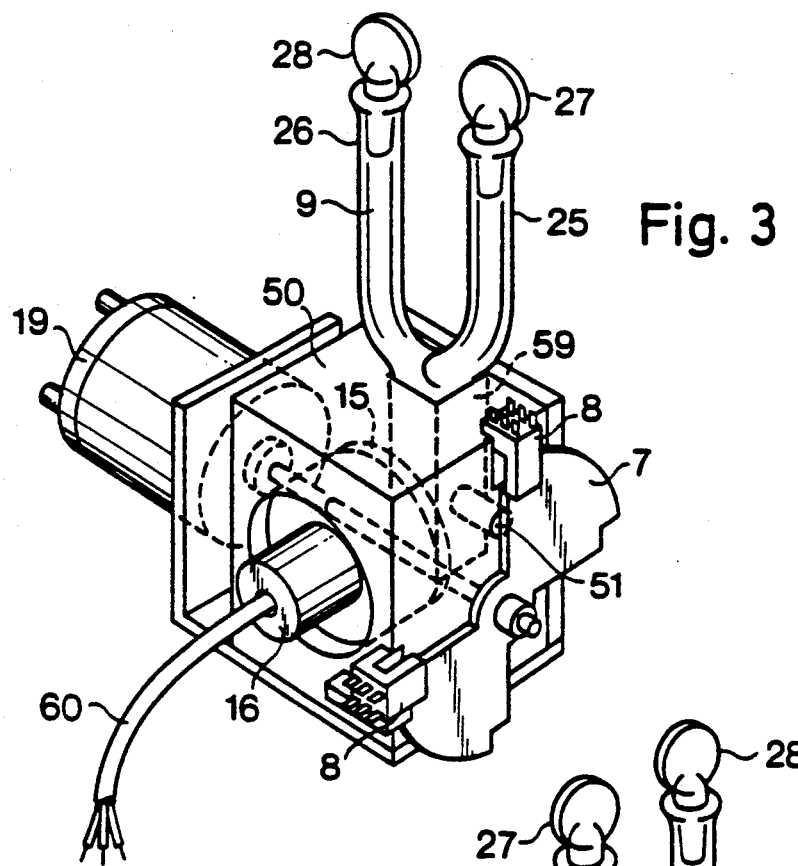
FIG. 3 is a detailed and perspective view of a measuring unit comprising the cell shown in FIG. 2a and further constituting part of the system shown in FIG. 1.

FIG. 3 illustrates the measuring unit of the schematic presentation of the test bench embodiment as shown in FIG. 1. The fluorescence cell 9 is received in a recess 59 of a black block 50 made from DELRIN. The sample contained in the fluorescence cell 9 is irradiated through a channel 51 of the block 50, which channel 51 is covered by the above-described chopper disc 7. In FIG. 3, the above-described components 8, 15, 16, 19 are also shown. Through a multicore cable 60, the signal obtained by the diode 16 is transmitted to the amplifier circuit 17 (not shown).

Figure 4:
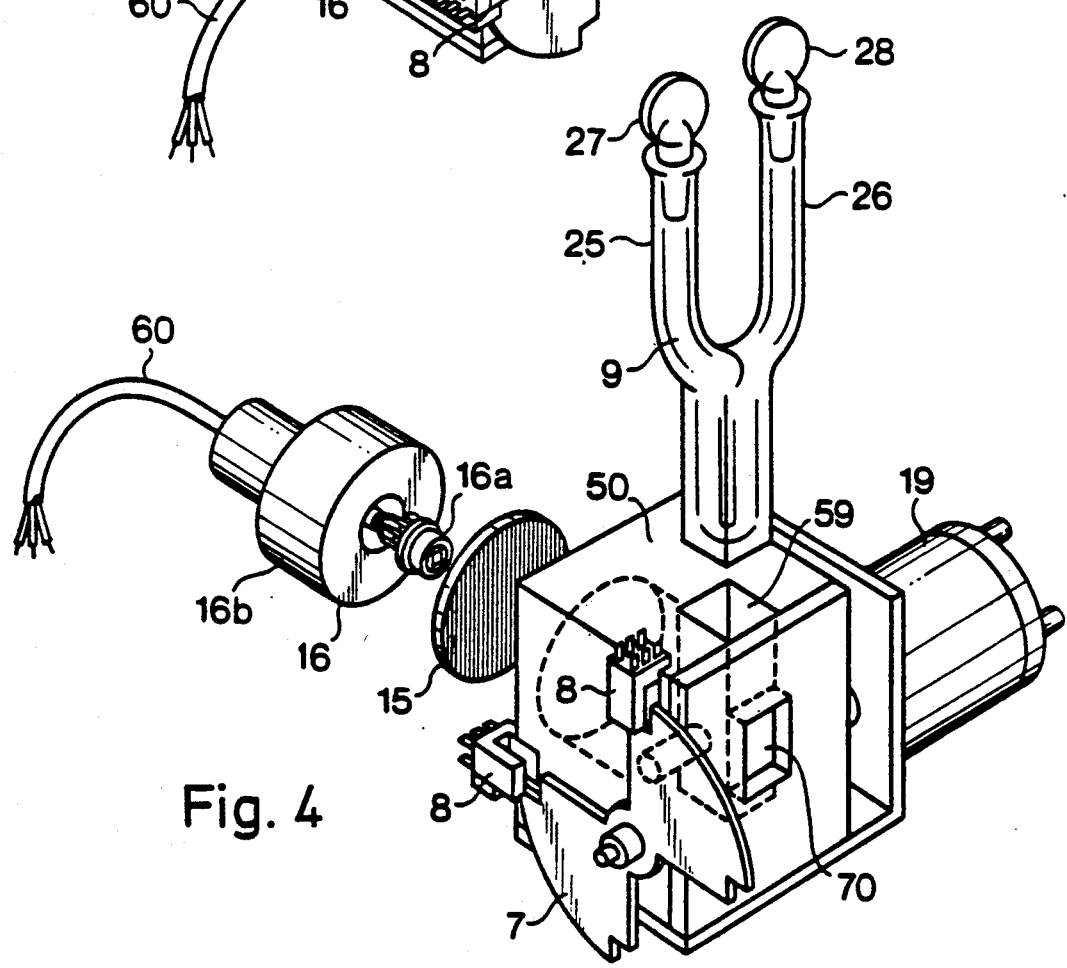
FIG. 4 is a detailed, perspective and partly exploded view of the measuring unit shown in FIG. 1.

FIG. 4 illustrates the measuring unit also illustrated in FIGS. 1 and 3. In FIG. 4, the 1270-nm sensitive diode 16 is exploded so that a diode part 16a and a container part 16b are shown. The fluorescence cell 9 has been pulled out. Through an opening 70 in the black block 50, luminescence of the sensitizing agent in the sample is emitted. In FIG. 4, the above-described components 7, 8, 15, 16, 19, 60 are also shown.

Figure 5:
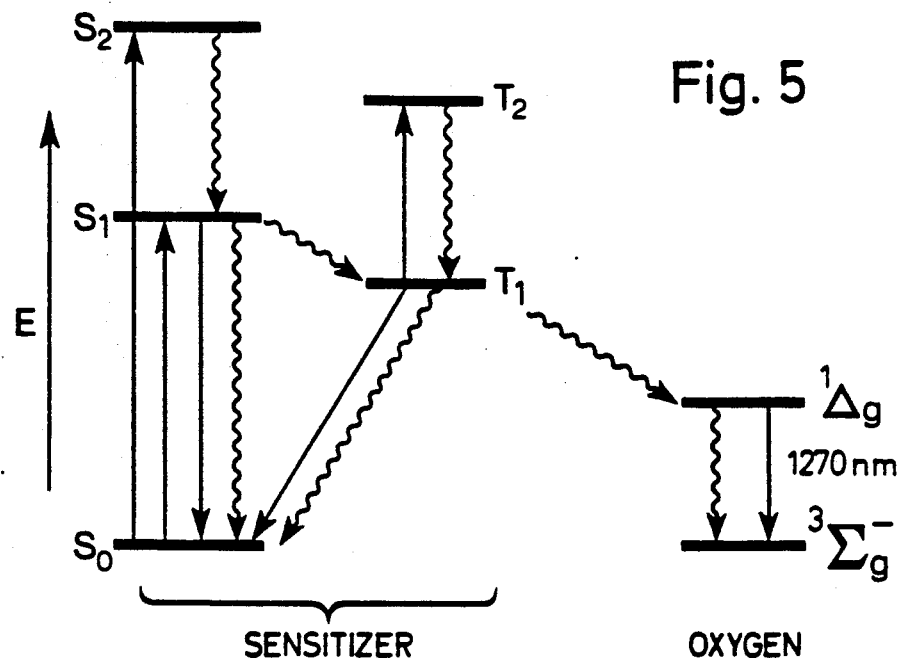
FIG. 5 is a diagrammatical view illustrating specific electronic states of a sensitizing agent and of molecular oxygen.

FIG. 5 illustrates the relationship between relevant electronic states of a sensitizing agent and an oxygen molecule, respectively, with regard to the energy content of each of these states. $S_0$, $S_1$ and $S_2$ designate the ground state, the first excited singlet state and the second excited singlet state of the sensitizing agent, respectively. Correspondingly, $T_1$ and $T_2$ designate the first excited triplet state and the second excited triplet state of the sensitizing agent, respectively. Radiative transitions between the individual electronic states are indicated by straight arrows and non-radiative transitions are indicated by wavy arrows. The electronic ground state and the excited singlet state of the oxygen molecule are designated $^3\Sigma_g^-$ and $^1\Delta_g$, respectively.

Figure 6:
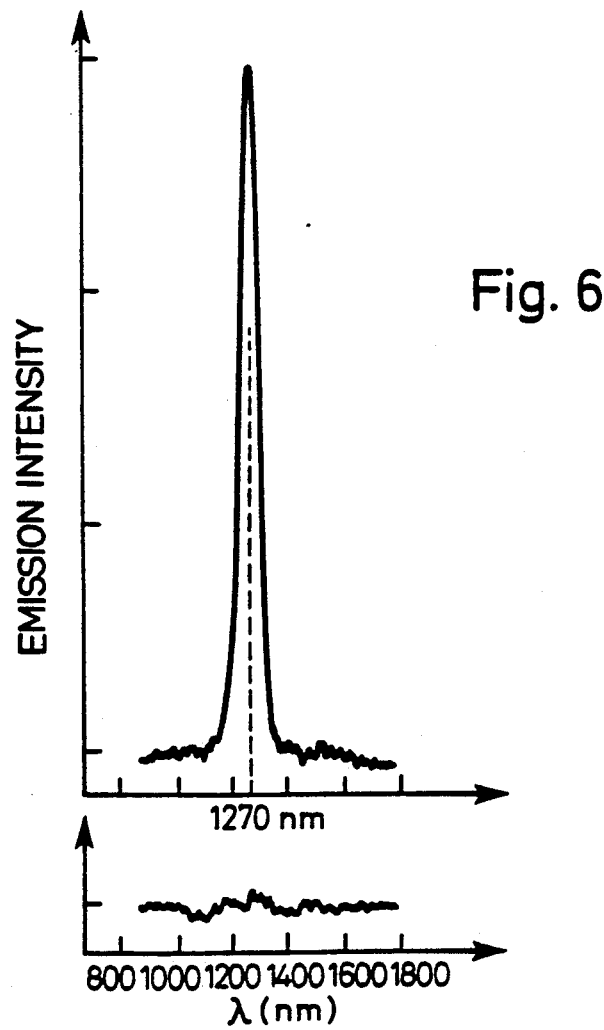
FIG. 6 is a diagrammatical view of an emission spectrum of singlet oxygen.
Figure 7:
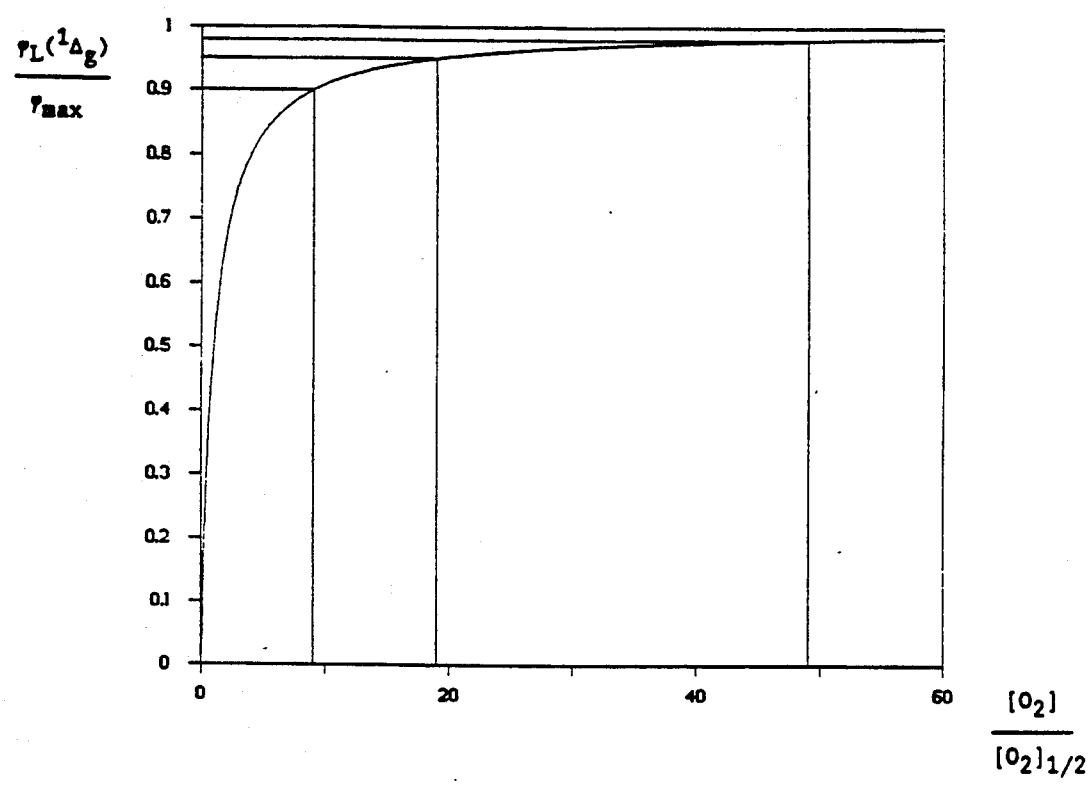
FIG. 7 is a diagrammatical view illustrating the course of the function $$\phi_L(^1\Delta_g)/\phi_{max} = \frac{[O_2]/[O_2]_{\frac{1}{2}}}{1 + [O_2]/[O_2]_{\frac{1}{2}}}$$

The upper part of FIG. 6 illustrates a typical 1270-nm emission spectrum obtained from an irradiated sensitizer-containing matrix in the presence of oxygen. The wavelengths at which the emission is measured are indicated in nm on the X-axis. The emission intensity of the sample is indicated in the Y-axis. The lower part of FIG. 6 illustrates the spectrum obtained from the matrix employed in the absence of oxygen.

The invention will now be further described by means of the following examples.

EXAMPLES

All chemicals, if not otherwise stated, were used as received without further purification.
Sensitizers and quenchers
Tetraphenylporphyrin ($H_2$TPP); zinc-tetraphenylporphyrin (ZnTPP), octaethylporphyrin ($H_2$OEP) and zinc-octaethylporphyrin (ZnOEP) were supplied by Porphyrin Products, Utah, USA.

Duroquinone and benzoquinone from Fluka were purified before use by sublimation and recrystallization, respectively. Tetraphenylbutadiene (TPB) was of scintillation grade.
Matrix components
Toluene (Uvasol) was supplied by Merck, PVC of the type BREON S110/10 was supplied by BP-Kemi, polycarbonate silicone of the type L.R. TM 3320 was supplied from General Electric, polyurethane of the type Desmopan was supplied by Bayer and cellulose acetate of the low viscosity and medium viscosity type was supplied by Serva. Tetrahydrofuran (THF) (p.a.) was supplied by Merck and stabilizers and other impurities were removed by passing the tetrahydrofuran through a column packed with basic alumina.
Oxygen source
The oxygen to be measured was in the form of $O_2$/Ar gas mixtures (from Strandmollen Industrigas A/S, Denmark). The actual concentration of oxygen was determined from the solubility of $O_2$ at 1 atm.

The term "aerated sample" means samples saturated with ambient atmospheric air.

METHODS

All experiments were performed at room temperature. Solutions were prepared and handled at subdued light, and they were stored in the dark at room temperature.

In Examples 1, 2 and 3, the samples to be investigated was contained in the 5×5 mm SUPRASIL fluorescence cell (Hellma), illustrated in FIG. 2a.

The principles of sample excitation and the detection of the resulting luminescence are illustrated in FIG. 1.

EXAMPLE 1

The use of zinc-octaethylporphin (ZnOEP) as a sensitizer for the formation of a singlet oxygen The following experiments were carried out to demonstrate the utility of ZnOPE as a sensitizer for the formation of singlet oxygen and to demonstrate the possibility of modifying the sensitizing excited state lifetime of ZnOPE by suitable quenchers so as to obtain a lifetime which is in a range affording a sufficient size variation over the oxygen concentration range to be measured,
1a) ZnOEP ZnOEP was dissolved in toluene so as to obtain a solution having a concentration of $2.3 \times 10^{-4}$M ZnOEP. The solution was placed in the SUPRASIL fluorescence cell illustrated in FIG. 2a and $O_2$/Ar gas mixtures of different oxygen concentrations were bubbled through the cell as described in connection with FIG. 2a. In this way, the ZnOEP solution was saturated with the gas. The excitation and the measuring of the 1270-nm luminescence was carried out as illustrated in FIG. 1. The oxygen concentration of the $O_2$/Ar gas mixtures employed were 0% 1%, 10%, 20.9% (the inherent $O_2$ concentration of atmospheric air), and 100%, respectively. The 1270-nm luminescence signals (in pA) corresponding to the varying oxygen concentrations which were obtained in the experiments are depicted in the upper curve of FIG. 8. As can be seen from this curve, the 1270-nm luminescence signal is saturated at an oxygen concentration corresponding to about 1% $O_2$, indicating a very high oxygen sensitivity. It may also be seen that the 1270-nm luminescence signal obtained from the aerated sample (20.9% $O_2$) is lower than what would be expected from the magnitude of the other signals. As discussed above, this phenomenon is presumed to be due to superoxide formation.

1b) ZnOEP in admixture with tetraphenylbutadiene

To decrease the oxygen sensitivity of the ZnOEP solution and thus make this solution useful for determining higher concentrations of oxygen, the sensitizing excited state lifetime of ZnOEP was reduced by addition of tetraphenylbutadiene. The $2.3 \times 10^{-4}$M ZnOEP solution was saturated with tetraphenylbutadiene and then diluted to obtain a ZnOEP solution half-saturated with tetraphenylbutadiene. The tetraphenylbutadiene-containing solution was then saturated with $O_2$/Ar gas mixtures of the same oxygen concentrations as stated above. The resulting 1270-nm luminescence signals (in pA) are depicted in the middle curve of FIG. 8. It is seen that the oxygen sensitivity is reduced, i.e. the 1270-nm luminescence signal increases with increasing oxygen concentrations within the total concentration range. Thus, the addition of tetraphenylbutadiene reduces the lifetime of the singlet oxygen sensitizing excited state of ZnOEP and it is possible to employ the ZnOEP/tetraphenylbutadiene sensitizing agent to measure oxygen concentrations in a range of about 0–760 mmHg, corresponding to 0–100%

1c) ZnOEP in admixture with duroquinone

The effect of using duroquinone as a quencher for the sensitizing excited state of ZnOEP was investigated. Duroquinone was added to the ZnOEP toluene solution to obtain a total concentration of duroquinone of $1.1 \times 10^{-2}$M. The above-mentioned $O_2$/Ar gas mixtures were employed and the resulting 1270-nm luminescence signals (in pA) are depicted in the lower curve of FIG. 8. It is seen that the oxygen sensitivity is further reduced as compared to the pure ZnOEP solution and the ZnOEP solution half-saturated with tetraphenylbutadiene.

Consequently, the ZnOEP/duroquinone sensitizing agent may be employed to measure oxygen concentrations in the range 0–760 mmHg, corresponding to 0–100% $O_2$. The actual sensitivity will depend on the concentration of duroquinone as illustrated in Examples 2b and 2c below where ZnTPP has been used as a sensitizer and subjected to quenching by different concentrations of duroquinone.

EXAMPLE 2

The use of zinc-tetraphenylporphin (ZnTPP) as a sensitizer for the formation of singlet oxygen 2a) ZnTPP Experiments corresponding to the experiments of Example 1, but using ZnTPP instead of ZnOEP, were carried out. A solution of $3.4 \times 10^{-4}$M ZnTPP in toluene was subjected to $O_2$/Ar gas mixtures of the oxygen concentrations stated in Example 1. The resulting 1270-nm luminescence signals are depicted in the upper curve of FIG. 9. It is seen that the oxygen sensitivity is even higher than the oxygen sensitivity obtained with the ZnOEP solution of Example 1a, i.e. the maximum luminescence signal is obtained at an oxygen concentration as low as 0.1%. The reduced 1270-nm luminescence signal obtained from an aerated sample (20.9% $O_2$) is lower than expected, and as with ZnOEP in Example 1a, it is presumed that this lower signal is due to superoxide formation.

2b) ZnTPP in admixture with $1.9 \times 10^{-3}$M duroquinone

Duroquinone was added to the ZnTPP solution to obtain a final concentration of duroquinone of $1.9 \times 10^{-3}$M. The resulting solution was subjected to $O_2$/Ar gas mixtures of the oxygen concentrations stated in Example 1a and the resulting 1270-nm luminescence signals are depicted in the middle curve of FIG. 9. It is seen that the oxygen sensitivity is reduced by addition of duroquinone which makes the solution useful for measuring oxygen in concentrations within a range of 0–760 mmHg, corresponding to 0–100%

2c) ZnTPP in admixture with $9.6 \times 10^{-3}$M duroquinone

The effect of increasing the concentration of duroquinone was investigated. A solution having a final concentration of duroquinone of $9.6 \times 10^{-3}$M was prepared and the solution was used for measuring oxygen of the concentrations stated in Example 1. The resulting 1270-nm luminescence signals are depicted in the lower curve of FIG. 9 and it is seen that the effect of increasing the duroquinone concentration is that the oxygen sensitivity is further reduced, and the magnitude of the 1270-nm luminescence signals is also reduced. Thus, by varying the duroquinone concentration in the ZnTPP solution, it is possible to adjust the oxygen sensitivity range to the particular measuring purpose.

EXAMPLE 3

The use of tetraphenylporphin ($H_2$TPP) as a sensitizer for the formation of singlet oxygen Experiments analogous to the experiments of Examples 1 and 2 were performed using $H_2$TPP as a sensitizer. A solution of $5.4 \times 10^{-4}$M $H_2$TPP in toluene was saturated with $O_2$/Ar gas mixtures of the oxygen concentrations stated in Example 1. Contrary to what was observed for the ZnOEP and ZnTPP solutions of Examples 1a and 2a, respectively, no reduction in the luminescence signal from the aerated sample was observed. In accordance with what has been stated above, this means that formation of superoxide is avoided. The fact that no superoxide is formed corresponds well to the above theoretical energy considerations, as the triplet state oxidation potential of $H_2$TPP is $-0.48$ V vs. SCE and thus higher than the presumed reduction potential of oxygen in the matrix.

The 1270-nm luminescence signals obtained are depicted in the upper curve of FIG. 10. As can be seen from the upper curve of FIG. 10, the oxygen sensitivity is high, as the maximum 1270-nm luminescence signal is already nearly obtained at an oxygen concentration of 1%.

By addition of benzoquinone in a concentration of $1.0 \times 10^{-2}$M to the $H_2$TPP toluene solution, it was attempted to reduce the oxygen sensitivity. As can be seen from the lower curve of FIG. 10, this oxygen sensitivity reduction was not obtained. What was obtained by the addition of benzoquinone was a decrease in the 1270-nm luminescence intensity, but no significant effect of the oxygen sensitivity.

EXAMPLE 4

Suitable sensitizing agent/matrix systems

As discussed above, the oxygen permeability of the matrix and the sensitizing excited state lifetime of the sensitizing agent determine the usefulness of a given sensitizing agent/matrix system with regard to particular molecular oxygen measurements.

In the present example, the phosphorescence intensity variation of the sensitizer phosphorescence has been used for establishing $[O_2]_{\frac{1}{2}}$ values of varying sensitizing agent/matrix systems. As discussed above, the $[O_2]_{\frac{1}{2}}$ value is the oxygen concentration at which 50% of the maximum luminescence yield, $\phi_{max}$, is obtained and is also the oxygen concentration at which a 50% quenching of the sensitizing excited states of the sensitizer is obtained. Consequently, the $[O_2]$ value resulting in 50% quenching of the sensitizer phosphoresence (i.e. the phosphorescence of the sensitizing excited states of the sensitizer) will be identical to the $[O_2]_{\frac{1}{2}}$ value of the 1270-nm singlet oxygen luminescence.

Various combinations of sensitizers and matrices were investigated with regard to their efficiency of oxygen quenching. Pd(II)- and Pt(II)-complexes of porphyrins were chosen because these complexes have strong phosphorescence at room temperature. The phosphorescence quenching of palladiumtetraphenylporphin (PdTPP), platinum-tetraphenylporphin (PtTPP) and their fluoro-substituted derivatives palladium(II)-tetra-(pentafluorophenyl)-porphyrin (PdTFPP) and platinum(II)-tetra-(pentafluorophenyl)-porphyrin (PtTFPP) by oxygen was investigated. The matrices used were PVC, polycarbonate/silicone, polyurethane and cellulose acetate.

The concentration of sensitizer in the matrix was in each case about 2 mg of sensitizer per 100 mg of matrix. The matrix component was mixed with the sensitizer in question and 100 mg of the resulting mixture was dissolved in 10 ml purified tetrahydrofuran (THF). The resulting solution was cast onto the surface of a hydrogen-fluoride-etched circular 19 mm diameter microscope glass cover slip supplied by Chance Propper Ltd. This microscope glass cover slip carrying the sensitizer/matrix will in the following be termed the probe. The probe was placed in the test set-up of FIG. 2b through which oxygen-containing fluids (i.e. liquid and gases) of varying oxygen concentrations were passed. The probe was excited by a spectrofluorophotometer of the type Shimadzu RF540, the spectrofluorophotometer used in Examples 1-3. The light of the spectrofluorophotometer filtered by a filter of the type GG 385 was at a wavelength of $\lambda_{ex}$ and the resulting phosphorescence intensity was measured at a wavelength of $\lambda_{em}$. Each of the wavelengths $\lambda_{ex}$ and $\lambda_{em}$, which have been used for the porphyrin in question, is specified in Table 1 below. The ambient oxygen concentrations corresponding to 50% phosphorescence quenching ($[O_2]_{\frac{1}{2}}$) are stated in Table 1 below.

TABLE 1

| Ambient oxygen concentrations (mmHg) at 50% quenching ($[O_2]_{\frac{1}{2}}$) | | | | | | |
|---|---|---|---|---|---|---|
| | | | | POLYMER (literature values of $O_2$-permeability in barrer) | | |
| POR-PHYRIN | $\lambda_{ex}$ in nm | $\lambda_{em}$ in nm | PVC (0.045) | Poly-carbonate/ silicone | Poly ure-thane | Cellu-lose acetate (0.68) |
| PdTPP $\tau > 800\ \mu s$ | 525 | 700 | ~61 | ~8 | <8 | <8 |
| PtTPP $\tau < 100\ \mu s$ | 511 | 667 | | ~38 | ~23 | ~38 |
| PdTFPP $\tau > 1000\ \mu s$ | 556 | 672 | ~34 | ~8 | | |
| PtTFPP $\tau < 100\ \mu s$ | 542 | 652 | ~460 | ~38 | ~38 | ~38 |

1 Barrer = $10^{-10}$ ml(STP) · cm$^2$/sec · cm$^2$ · cmHg.
$\tau$ = the sensitizing excited state lifetime.
NB: Only the $O_2$ permeability values of PVC and cellulose acetate are stated as reliable $O_2$ permeability values of polycarbonate/silicone and polyurethane are unavailable.

The $[O_2]_{\frac{1}{2}}$ values of 8 mmHg and 61 mmHg, obtained for PdTPP in polycarbonate/silicone and PVC, respectively, may be compared with the $[O_2]_{\frac{1}{2}}$ values of PdTPP in toluene of less than 1.5 mmHg. When comparing the results of the experiments in which PVC (of a lower oxygen permeability) and cellulose acetate (of a higher oxygen permeability) have been tested, it is seen that the matrix of the lower oxygen permeability (PVC) results in the highest $[O_2]_{\frac{1}{2}}$ values and generally the oxygen permeability of the matrix is a critical parameter of the efficiency of oxygen quenching for a given sensitizer. Further, it is seen from the results of Table 1 that the sensitizing excited state lifetime of the sensitizer is critical, i.e. sensitizers of the shorter sensitizing excited state lifetimes (PtTPP and PtTFPP) result in higher $[O_2]_{\frac{1}{2}}$ values, whereas sensitizers of longer sensitizing excited state lifetimes result in lower $[O_2]_{\frac{1}{2}}$ values.

Based on the fact that the sensitizing excited state lifetimes (in this case the triplet state lifetimes) of PdTPP and of PdTFPP at room temperature are typical for porphyrins and Zn(II)-complexes of porphyrins and based on the results stated in Table 1, it is contemplated that octaethylporphyrin (H$_2$OEP), tetraphenylporphyrin (H$_2$TPP), tetra(pentafluorophenyl)-porphyrin (H$_2$TFPP), tetrabenzoporphyrin (H$_2$TBP), alkyl- and aryl-substituted tetrabenzoporphyrins and the Zn(II)-complexes of these may advantageously be employed in combination with a matrix constituted of PVC as the above-stated results indicate that the quantum yield of singlet oxygen formation ($\phi_{et}$) will be 0.5 for oxygen concentrations of about 38 mmHg.

Likewise, tetraphenylporphyrins substituted with bromine and metal complexes thereof are expected to be useful when using e.g. cellulose acetate as matrix. Furthermore, it will be understood that the results of Table 1 will also be useful as a guideline for selection of sensitizer/matrix systems for use in the luminescence quenching methods of the prior art.

I claim:
1. A method of determining the concentration of ground state molecular oxygen in a test sample, said method comprising:
(a) exciting oxygen molecules of the test sample from the electronic ground state to the excited $^1\Delta_g$ state (excited singlet state),
(b) measuring a 1270-nm luminescence characteristic of the excited oxygen molecules in the test sample,
(c) quantitatively correlating the measured 1270-nm luminescence characteristic with standard values determined on the basis of a positive quantitative correlation between (i) 1270-nm luminescence signals of excited oxygen molecules in reference samples having known, pre-selected concentrations of ground state molecular oxygen and (ii) the concentrations of ground state molecular oxygen in the reference samples, and (d) quantifying the content of ground state molecular oxygen in the test sample on the basis of the quantitative correlation of the measured 1270-nm luminescence characteristic with the standard values.

2. A method according to claim 1 wherein the 1270-nm luminescence characteristic is the 1270-nm luminescence intensity.

3. A method according to claim 1 wherein the excitation of the ground state oxygen molecules is performed by means of a sensitizing agent having an excited electronic state (sensitizing excited state) capable of exciting molecular oxygen from the electronic ground state to the excited singlet state, the sensitizing agent being in diffusion contact with the sample.

4. A method according to claim 3 wherein the energy of the excited state of the sensitizing agent is higher than 0.98 eV.

5. A method according to claim 3 wherein the sensitizing agent comprises a sensitizer having an excited state capable of exciting molecular oxygen from the electronic ground state to the excited singlet state and a quencher capable of deactivating the excited state of the sensitizer so as to reduce the excited state lifetime of the sensitizer, the quencher being in diffusion contact with the sensitizer.

6. A method according to claim 3 wherein the sensitizing excited state of the sensitizing agent is the excited triplet state.

7. A method according to claim 3 wherein the diffusion contact between the sensitizing agent and the sample is established at an interface between the sensitizing agent and the sample.

8. A method according to claim 3 wherein the oxidation potential of the excited state of the sensitizing agent is of a size which essentially renders the sensitizing agent incapable of converting molecular oxygen to the superoxide.

9. A method according to claim 8 wherein the oxidation potential of the excited state of the sensitizing agent is higher than $-0.7$ V versus saturated Calomel Electrode.

10. A method according to claim 3 wherein the sensitizing agent is selected from the group consisting of porphyrins and porphyrin-related compounds.

11. A method according to claim 10 wherein the sensitizing agent is selected from the group consisting of metal-free porphyrins, metallo-porphyrins, phtalocyanins, metallo-phtalocyanins and derivatives thereof.

12. A method according to claim 3 wherein the sensitizing agent is embedded in a matrix.

13. A method according to claim 12 wherein the matrix comprises an organic solvent.

14. A method according to claim 12 wherein the matrix in which the sensitizing agent is embedded is free of OH-groups so as to maximize the luminescence intensity of excited singlet oxygen.

15. A method according to claim 12 wherein the diffusion contact between the sensitizing agent and the sample is established through a membrane which separates said matrix containing the sensitizing agent and the sample containing the ground state molecular oxygen to be measured.

16. A method according to claim 12 wherein the matrix comprises a polymer.

17. A method according to claim 12 wherein the sensitizing agent and the matrix in which it is present are selected so as to affect the excited state lifetime of the sensitizing agent and the oxygen permeability of the matrix to thereby obtain a luminescence characteristic of a sufficient size variation over the ground state oxygen concentration range to be measured.

18. A method according to claim 17 wherein the sensitizing agent and the matrix in which it is present are adapted to a particular maximum ambient oxygen concentration to be measured so that a matrix oxygen concentration of at the most $50 \bullet [O_2]_i$ will be obtained on contacting the matrix with a sample of the particular maximum ambient ground state oxygen concentration.

19. A method according to claim 18 wherein a matrix oxygen concentration of at the most $20 \bullet [O_2]_i$ is obtained.

20. A method according to claim 18 wherein a matrix oxygen concentration of at the most $10 \bullet [O_2]_i$ is obtained.

21. A method according to claim 3 wherein the excited state of the sensitizing agent is formed from another electronic state of the sensitizing agent by absorption of electromagnetic radiation.

22. A method according to claim 21 wherein the electromagnetic radiation is of a wavelength of less than 1270 nm.

23. A method according to claim 22 wherein the electromagnetic radiation is of a wavelength in the range of 300–1000 nm.

24. A method according to claim 22 wherein the sensitizing agent is selected from transition metal complexes.

25. A method according to claim 24 wherein the sensitizing agent is selected from the group consisting of complexes of Zn(II), Pd(II), Pt(II), Ru(II) and Os(II).

26. A method of determining the concentration of ground state molecular oxygen in a test sample which is a fluid sample of biological origin having a molecular oxygen concentration at a physiological level, said method comprising:

(a) exciting oxygen molecules of the test sample from the electronic ground state to the excited $^1\Delta_g$ state (excited singlet state), (b) measuring a 1270-nm luminescence characteristic of the excited oxygen molecules in the test sample, (c) quantitatively correlating the measured 1270-nm luminescence characteristic with standard values determined on the basis of a positive quantitative correlation between (i) 1270-nm luminescence signals of excited oxygen molecules in reference samples having known, pre-selected concentrations of ground state molecular oxygen and (ii) the concentrations of ground state molecular oxygen in the reference samples, and (d) quantifying the content of ground state molecular oxygen in the test sample on the basis of the quantitative correlation of the measured 1270-nm luminescence characteristic with the standard values.

27. A method according to claim 26 wherein the fluid sample of biological origin is blood.

28. A method according to claim 26 wherein the fluid sample is an oxygen-containing gas of biological origin.

29. A system for determining the concentration of ground state molecular oxygen in a test sample, said system comprising:

(a) means for exciting oxygen molecules of the test sample from the electronic ground state to the excited $^1\Delta_g$ state (excited singlet state), said means comprising an electromagnetic radiation source and a sensitizing agent, said sensitizing agent being in diffusion contact with the sample, (b) means for measuring a 1270-nm luminescence characteristic of the excited oxygen molecules in the test sample, and (c) means for quantifying the content of ground state molecular oxygen in the test sample based on a quantitative correlation of the measured 1270-nm luminescence characteristic with standard values determined on the basis of a positive quantitative correlation between (i) 1270-nm luminescence signals of excited oxygen molecules in reference samples having known, pre-selected concentrations of ground state molecular oxygen and (ii) the concentrations of ground state molecular oxygen in the reference samples.

30. A system according to claim 29 wherein the sensitizing agent is embedded in a matrix, the matrix being an organic solvent.

31. A system according to claim 29 wherein said means for quantifying comprises a signal or data processing means.

32. A system according to claim 29 wherein the sensitizing agent has an excited electronic state capable of exciting molecular oxygen from the electronic ground state to the excited singlet state.

33. A system according to claim 32 wherein the sensitizing agent has an excited electronic state, the energy of which is higher than 0.98 eV.

34. A system according to claim 29 wherein the electromagnetic radiation is of a wavelength of less than 1270 nm.

35. A system according to claim 34 wherein the electromagnetic radiation is of a wave length in the range of 300–1000 nm.

36. A system according to claim 29 wherein the means for measuring a 1270-nm luminescence characteristic of the excited oxygen molecules comprises a detector being capable of measuring said luminescence characteristic at a wavelength of about 1270 nm.

37. A system according to claim 36, wherein said detector is covered by a filter.

38. A system according to claim 36 wherein said detector is connected to an amplifier circuit.

39. A system according to claim 29 wherein the sensitizing agent is embedded in a matrix.

40. A system according to claim 39 wherein the sensitizing agent and the matrix in which it is present are selected so as to affect the excited state lifetime of the sensitizing agent and the oxygen permeability of the matrix to thereby obtain a luminescence characteristic of a sufficient size variation over the ground state oxygen concentration range to be measured.

41. A system according to claim 39 wherein the diffusion contact between the sensitizing agent and the sample is established through a membrane which separates said matrix containing the sensitizing agent and the sample containing the ground state molecular oxygen to be measured.

42. A system according to claim 39 wherein the matrix is a polymer which is free of OH groups.

* * * * *

UNITED STATES PATENT AND TRADEMARK OFFICE
CERTIFICATE OF CORRECTION

PATENT NO. : 5,242,835
DATED : September 7, 1993
INVENTOR(S) : Niels-Henrik Jensen It is certified that error appears in the above-identified patent and that said Letters Patent is hereby corrected as shown below:

Column 26, line 5, delete "as to affect" insert --that--.

Column 28, line 20, delete "as to affect" insert --that--.

Column 28, line 22, delete "to thereby obtain" insert --will provide--.

Signed and Sealed this

Seventeenth Day of May, 1994

Attest:

BRUCE LEHMAN

Attesting Officer

Commissioner of Patents and Trademarks